(12) United States Patent
Kawamura

(10) Patent No.: US 9,119,915 B2
(45) Date of Patent: Sep. 1, 2015

(54) INFUSION PUMP SYSTEM

(75) Inventor: Yasuhiro Kawamura, Tokyo (JP)

(73) Assignee: SIMS, Tokyo (JP)

( * ) Notice: Subject to any disclaimer, the term of this patent is extended or adjusted under 35 U.S.C. 154(b) by 646 days.

(21) Appl. No.: 13/063,751

(22) PCT Filed: Sep. 9, 2009

(86) PCT No.: PCT/JP2009/065708
§ 371 (c)(1),
(2), (4) Date: May 19, 2011

(87) PCT Pub. No.: WO2010/029931
PCT Pub. Date: Mar. 18, 2010

(65) Prior Publication Data
US 2012/0265125 A1    Oct. 18, 2012

(30) Foreign Application Priority Data

Sep. 12, 2008 (JP) .................. 2008-234866

(51) Int. Cl.
| A61M 5/168 | (2006.01) |
| A61M 5/142 | (2006.01) |
| A61M 5/14 | (2006.01) |
| G06F 19/00 | (2011.01) |

(52) U.S. Cl.
CPC .......... *A61M 5/16804* (2013.01); *A61M 5/142* (2013.01); *A61M 5/1407* (2013.01); *A61M 5/1411* (2013.01); *A61M 5/16827* (2013.01); *A61M 5/16877* (2013.01); *A61M 5/16886* (2013.01); *G06F 19/3468* (2013.01); *A61M 2005/14208* (2013.01); *A61M 2205/0294* (2013.01); *A61M 2205/3553* (2013.01); *A61M 2205/3592* (2013.01); *A61M 2205/50* (2013.01); *A61M 2205/52* (2013.01); *A61M 2206/22* (2013.01); *G06F 19/3418* (2013.01)

(58) Field of Classification Search
CPC .......... A61M 5/1407; A61M 5/16827; A61M 5/16886; A61M 2005/14208; A61M 2205/3592; A61M 5/142; A61M 5/16804; A61M 5/1411; A61M 5/16877; A61M 2205/0294; A61M 2205/3553; A61M 2205/50; A61M 2205/52; A61M 2206/22; G06F 19/3468; G06F 19/3418
USPC .................. 604/890–892.1, 65–67, 131, 151; 600/431
See application file for complete search history.

(56) References Cited

U.S. PATENT DOCUMENTS

| 5,782,805 A | 7/1998 | Meinzer et al. |
| 2004/0051368 A1 | 3/2004 | Caputo et al. |

(Continued)

FOREIGN PATENT DOCUMENTS

EP    1433456 A1    6/2004

OTHER PUBLICATIONS

European Patent Office, European Search Report dated May 18, 2012 in European Patent Application No. EP09813077, 15 pages.

*Primary Examiner* — Theodore Stigell
(74) *Attorney, Agent, or Firm* — Inskeep IP Group, Inc.

(57) ABSTRACT

There is provided an infusion pump system for delivering a predetermined medical solution at a preset reference infusion speed. The system comprises a medical solution container; an infusion line through which the medical solution is drawn out of the medical solution container; an infusion pump configured to discharge the medical solution via the infusion line. The infusion pump is controlled so that the discharge speed of the infusion pump is computed on the basis of a current discharge speed of the infusion pump and the infusion speed of the medical solution, the resulting discharge speed is corrected by a predefined correction coefficient, and the medical solution is discharged at the corrected discharge speed.

18 Claims, 21 Drawing Sheets

(56) References Cited

U.S. PATENT DOCUMENTS

| | | | |
|---|---|---|---|
| 2010/0192686 A1* | 8/2010 | Kamen et al. | 73/290 R |
| 2010/0209267 A1* | 8/2010 | Davis | 417/412 |
| 2011/0264071 A1* | 10/2011 | Braig et al. | 604/504 |
| 2011/0313318 A1* | 12/2011 | Rule et al. | 600/581 |
| 2012/0218740 A1* | 8/2012 | Estes et al. | 362/101 |
| 2012/0226446 A1* | 9/2012 | Nelson et al. | 702/25 |
| 2012/0238997 A1* | 9/2012 | Dewey | 604/500 |
| 2012/0259282 A1* | 10/2012 | Alderete et al. | 604/131 |

* cited by examiner

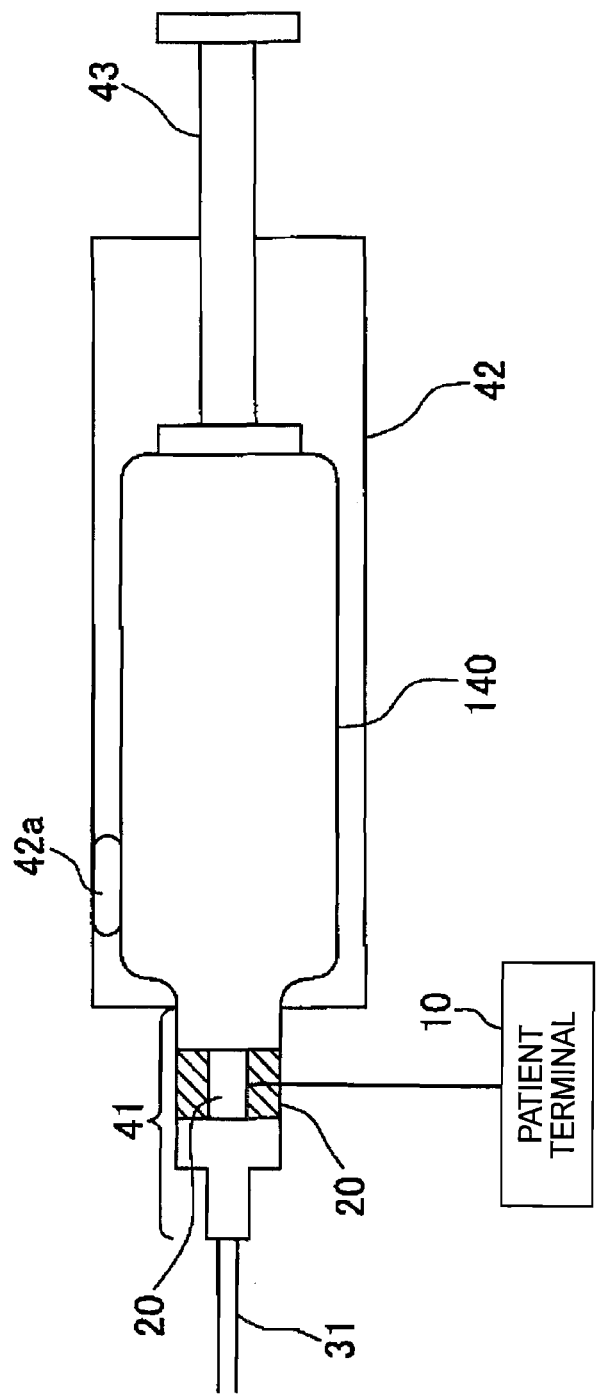

INFUSION PUMP SYSTEM

RELATED APPLICATIONS

This application claims priority to International Patent Application No. PCT/JP2009/065708, International Filing Date Sep. 9, 2009, entitled Infusion Pump System, which claims priority to Japanese Patent Application No. JP2008-234866 filed Sep. 12, 2008 entitled Infusion Pump System, the contents of both of which are incorporated in their entireties herein.

TECHNICAL FIELD

The present invention relates to an infusion pump system used in the field of medical treatment for delivery (i.e., infusion or delivery of fluid) of a liquid medication into a body of a patient, and in particular to an infusion pump system configured for automatic infusion of the liquid medication at a preset reference infusion speed or automatic infusion to be completed within a preset infusion completion time.

BACKGROUND ART

An example of the above infusion pump system is disclosed in the patent literature PTL 1 filed by the inventor of the present invention. The infusion pump system of PTL 1 comprises (a) an infusion bag (as a medical solution container) containing a predetermined medical solution; (b) an infusion tube (as an infusion line) connected to the infusion bag and configured for drawing of the medical solution drawn therethrough and out of the infusion bag; (c) a pump unit driven by a piezoelectric element and configured to discharge the medical solution via the infusion tube; (d) an operation panel for inputting setting values including a volume of infusion (as an infusion speed) or a total volume of infusion; and (e) a control circuit.

The control unit includes (i) a settings switching part configured to select the setting values of the volume of infusion or the total volume of infusion that have been input; (ii) a flow measurement part configured to measure an infusion speed of the medical solution flowing through the infusion tube; (iii) a comparison part configured to compare the setting value of the volume of infusion with the measured infusion speed; and (iv) a pump control part configured to control the pump unit on the basis of the result of comparison by the comparison part.

In this infusion pump system, the setting value of the volume of infusion (a reference infusion speed) is input by operating the operation panel, and the discharge speed of the pump unit is controlled by the control circuit with reference made to (i) the setting value of the volume of infusion and (ii) the infusion speed of the medical solution flowing through the infusion tube. The control is made such that the infusion speed of the medical solution becomes equal to the setting value and thereby infusion is automatically done with a predefined volume of infusion, in other words, at a predefined infusion speed.

The configuration and operation of the infusion pump in the above-described infusion pump system is described below with reference to FIG. 5.

Referring to FIG. 5, there is schematically illustrated a piezoelectric pump provided in the pump unit. The pump unit 20 (infusion pump) includes a piezoelectric pump unit 21 constructed by a plurality of the piezoelectric pumps 22 arranged in series with each other, in parallel with each other, or in combination of series and parallel connections.

The piezoelectric pump 22 includes a piezoelectric element 221; an electrode 222 disposed upon and in close contact with the piezoelectric element 221; a glass plate 223 configured to be placed in oscillation by the piezoelectric element 221 in a direction indicated by an arrow S; a chamber 224 containing the medical solution; an inlet hole 225 through which the medical solution is drawn into the chamber 224; and an outlet hole 226 via which the medical solution is discharged from the chamber 224.

The piezoelectric element 221 in the piezoelectric pump 22 is adapted to oscillate in accordance with voltage and frequency applied to the electrode 222, and the glass plate 223 is adapted to oscillate in response to the oscillation of the piezoelectric element 221. As a result, the volume of the chamber 224 changes.

When the volume of the chamber 224 is reduced by the oscillation of the glass plate 223, the inlet hole 225 becomes smaller (more restricted) than the outlet hole 226. Accordingly, the flow resistance P2 created in the medical solution flowing toward the outlet hole 226 becomes smaller than the flow resistance P1 created in the medical solution flowing toward the inlet hole 225. As a result, the medical solution in the chamber 224 flows from the inlet hole 225 to the outlet hole 226 (in a direction indicated by an arrow R).

When the volume of the chamber 224 is increased by the oscillation of the glass plate 223, the medical solution is drawn via the inlet hole 225 into the chamber 224, and the piezoelectric element 221 is placed in desired oscillation by adjustment of the voltage and frequency applied to the electrode 222, so that the medical solution is discharged via the outlet hole 226 at a desired discharge speed. In this manner, the medical solution discharged via the outlet hole 226 of the piezoelectric pump 22 is infused via the infusion tube 31 into an inside of a body of a patient H such as a blood vessel IV (vein).

Since the above-described piezoelectric pump 22 has an open structure (i.e., has a flow path extending in a continuous manner without intervening valves provided therein), the discharge speed is susceptible to be influenced by a destination of discharging of the medical solution. For example, if the destination of the discharging of the medical solution is the vein, then a venous pressure created in the vein acts as the flow resistance P3 upon the medical solution. Even when predefined voltage and frequency are applied to the electrode 222 by the control circuit such that the discharge speed of the piezoelectric pump 22 becomes equal to the setting value of the volume of infusion, there may exist a gap between the medical solution delivered (infused) to the vein and the setting value of the volume of infusion.

Also, in the above-described infusion pump system, if there is the gap between the setting value of the preselected volume of infusion and the actual measurement of the infusion speed, the control circuit is configured to automatically change the discharge speed of the piezoelectric pump (i.e., the pump unit) so that the infusion speed of the medical solution becomes equal to the setting value of the volume of infusion.

CITATION LIST

Patent Literature

PTL 1: Japanese Patent Application Laid-Open Publication No. 2006-136376

SUMMARY OF THE INVENTION

Technical Problem

Downside to the above system is that, if an abnormal state occurs in the system or in the patient causing in a short period of time a large gap between the setting value of the preselected volume of infusion and the measured infusion speed of the medical solution, the control circuit automatically attempts to eliminate the gap and substantially change the discharge speed of the pump unit. As a result, the infusion speed of the medical solution is changed substantially causing undesirable effects upon conditions of the patient.

In particular, in a case of infusion of the medical solution having substantial effects with small dosage, rapid change in the infusion speed could expose the patient to serious problems or risks. The same or similar problems may occur when a pump unit other than the piezoelectric pump is in use.

In order to solve the problems associated with the above-identified drawbacks, an object of the present invention is to provide an infusion pump system that ensures further safety improvement.

Solution to Problem

In order to attain the above-identified objective, a first aspect of the present invention provides an infusion pump system for infusion of a predetermined medical solution at a preset reference infusion speed, whose basic configuration is schematically illustrated in FIG. 1.

The infusion pump system according to the first aspect comprises (A) a medical solution container; (B) an infusion line; (C) an infusion pump 20; (D) a reference infusion speed storing unit 12c; (E) a correction coefficient storing unit 12a; (F) an infusion speed measurement unit; (G) a discharge speed computation unit; (H) a discharge speed correction unit 11b; and (I) a control unit 11c.

The medical solution container is configured to contain the medical solution. Also, the medical solution is drawn out of the medical solution container via the infusion line.

The infusion pump 20 is configured to discharge the medical solution via the infusion line.

The reference infusion speed storing unit 12c is configured to store the reference infusion speed.

The correction coefficient storing unit 12a is configured to store a correction coefficient. The correction coefficient is used to correct a variation in a discharge speed of the medical solution. Also, the correction coefficient is predefined in accordance with a degree of medical effect of the medical solution.

The infusion speed measurement unit 11d is configured to measure an infusion speed of the medical solution flowing through the infusion line.

The discharge speed computation unit 11a1 is configured for discharge speed computation. In the discharge speed computation, a discharge speed of the infusion pump 20 for infusion of the medical solution at the reference infusion speed is computed. The discharge speed computation is made at predetermined intervals and with reference to (i) a current discharge speed of the infusion pump 20, (ii) the reference infusion speed stored in the reference infusion speed storing unit 12c, and (iii) the infusion speed of the medical solution measured by the infusion speed measurement unit 11d.

The discharge speed correction unit 11b is configured for discharge speed correction; in the discharge speed correction, the discharge speed that has been obtained as a result of the discharge speed computation by the discharge speed computation unit 11a1 is corrected. The discharge speed correction is made with reference to (i) the current discharge speed of the infusion pump 20 and (ii) the correction coefficient for the medical solution stored in the correction coefficient storing unit 12a.

The control unit 11c is configured to control the infusion pump 20 to make the infusion pump 20 discharge the medical solution at the discharge speed that has been obtained as a result of the discharge speed correction by the discharge speed correction unit 11b.

In order to attain the above-identified aim, a second aspect of the present invention provides an infusion pump system for infusion of a predetermined medical solution within a predefined infusion completion time, whose basic configuration is illustrated in FIG. 2.

The infusion pump system according to the second aspect comprises: (A) a medical solution container; (B) an infusion line; (C) an infusion pump 20; (D) a correction coefficient storing unit 12a; (E) a remaining amount detection unit 11e; (F) a remaining time measurement unit 11f; (G) a discharge speed computation unit 11a2; (H) a discharge speed correction unit 11b; and (I) a control unit 11c.

The medical solution container is configured to contain the medical solution. Also, the medical solution is drawn out of the medical solution container via the infusion line.

The infusion pump 20 is configured to discharge the medical solution via the infusion line.

The correction coefficient storing unit 12a is configured to store a correction coefficient. The correction coefficient is used for correction of a variation in a discharge speed of the medical solution. The correction coefficient is predefined in accordance with a degree of medical effect of the medical solution.

The remaining amount detection unit 11e is configured to detect a remaining amount of the medical solution.

The remaining time measurement unit 11f is configured to measure a remaining time before the infusion completion time is reached.

The discharge speed computation unit 11a2 is configured for discharge speed computation. In the discharge speed computation, a discharge speed of the infusion pump 20 for infusion of the medical solution within the infusion completion time is computed. The discharge speed computation is made with reference to (i) the remaining amount of the medical solution detected by the remaining amount detection unit 11e and (ii) the remaining time before the infusion completion time is reached measured by the remaining time measurement unit 11f.

The discharge speed correction unit 11b is configured for discharge speed correction. In the discharge speed correction, the discharge speed obtained as a result of the discharge speed computation by the discharge speed computation unit 11a1 is corrected. The discharge speed correction is made with reference to (i) a current discharge speed of the infusion pump 20 and (ii) the correction coefficient for the medical solution stored in the correction coefficient storing unit 12a.

The control unit 11c is configured to control the infusion pump 20 to make the infusion pump 20 discharge the medical solution at the discharge speed that has been obtained as a result of the discharge speed correction by the discharge speed correction unit 11b.

According to a third aspect of the present invention, the infusion pump system according to the first or second aspect further comprises, as illustrated in FIG. 1 or FIG. 2 depicting the basic configuration thereof, (a) an information input unit 17, a medical solution information storing unit 12b, an infusion speed range computation unit 11g; and a safe operation unit 11h.

Information on an infusion target into which the medical solution is to be infused is input into the information input unit 17.

The medical solution information storing unit 12b is configured to store usage and dosage of the medical solution.

The infusion speed range computation unit 11g is configured for infusion speed range computation. In the infusion speed range computation, an allowable range of the infusion speed is computed for the medical solution. The infusion speed range computation is made with reference to (i) the information input into the information input unit 17 and (ii) the usage and dosage of the medical solution stored in the medical solution information storing unit 12b.

The safe operation unit 11h is configured to perform a predefined safe operation when the discharge speed corrected by the discharge speed correction unit 11b does not fall within the allowable range of the infusion speed for the medical solution computed by the infusion speed range computation unit 11g.

According to a fourth aspect of the present invention, which is in the context of the third aspect, as illustrated in FIG. 1 or FIG. 2 depicting the basic configuration thereof, the safe operation unit 11h is configured to trigger an alarm.

According to a fifth aspect of the present invention, which is in the context of the third or fourth aspect, as illustrated in FIG. 1 or FIG. 2 depicting the basic configuration thereof, the safe operation unit 11h is configured to control the infusion pump 20 to make the infusion pump 20 discharge the medical solution at the discharge speed corrected by the discharge speed correction unit 11b.

According to a sixth aspect of the present invention, which is in the context of the third or fourth aspect, as illustrated in FIG. 1 or FIG. 2, the safe operation unit 11h is configured to halt the infusion pump 20 discharging the medical solution.

According to a seventh aspect of the present invention, the infusion pump 20 of the infusion pump system according to any one of the first to sixth aspect comprises a piezoelectric pump unit comprising at least one piezoelectric pump driven by a piezoelectric element.

According to an eighth aspect of the present invention, the infusion pump system of the infusion pump system according to the seventh aspect includes a plurality of the piezoelectric pump units arranged in parallel with each other; a plurality of entry tubes via which the piezoelectric pump units are individually connected to the infusion line, the entry tubes having a cross section smaller than that of the infusion line; and a bypass tube configured to connect the entry tubes to each other.

According to a ninth aspect of the present invention, which is in the context of the eighth aspect, the infusion pump 20 comprises a plurality of groups of the piezoelectric pump units, and the control unit 11c is configured to use different discharge timings to individually control the groups of the piezoelectric pump units.

According to a tenth aspect of the present invention, which is in the context of the seventh aspect, a plurality of the medical solution containers each contains a corresponding each of a plurality of the medical solutions, and a corresponding each of the medical solutions is drawn out of the corresponding each of the medical solution containers via each of a plurality of the infusion lines.

The infusion pump 20 includes one piezoelectric pump unit and a plurality of the entry tubes each connecting a corresponding each of the infusion lines to the piezoelectric pump unit, and a plurality of cut-off valves each provided in a corresponding each of the entry tubes and configured to block the medical solution drawn via the infusion line into the piezoelectric pump unit The control unit 11c is configured to control opening and closing of the cut-off valves such that predefined amounts of the medical solutions are drawn into the piezoelectric pump unit from corresponding each of the entry tubes.

According to an eleventh aspect of the present invention, which is in the context of the tenth aspect, the control unit 11c is configured to close one of the cut-off valves when a predefined negative pressure avoidance time has elapsed after opening of an other of the cut-off valves.

According to a twelfth aspect of the present invention, which is in the context of the tenth or eleventh aspect, the control unit 11c is configured to intermittently open and close at least one of the cut-off valves each provided in corresponding each of the entry tubes.

According to a thirteenth aspect of the present invention, which is in the context of the tenth or eleventh aspect, the infusion pump system further comprises a biometric information input unit 17 into which biometric information is input. The biometric information is measured in the infusion target into which the medical solution is infused. Also, the control unit 11c is configured to open and close a selected one of the cut-off valves on the basis of the biometric information input to the biometric information input unit 17.

According to a fourteenth aspect of the present invention, the infusion pump system according to any one of the first to thirteenth aspect further comprises a bypass unit configured to discharge the medical solution via the infusion line, the bypass unit bypassing the infusion pump 20.

According to a fifteenth aspect of the present invention, which is in the context of any one of the first to ninth aspect, the infusion pump 20 is arranged inside of the medical solution container such that the infusion pump 20 is positioned inward with reference to the medical solution exit portion via which the infusion line is attached to the medical solution container.

According to a sixteenth aspect of the present invention, the infusion pump system according to the fifteenth aspect further comprises a cylinder accommodating therein a medical solution container made of a flexible material; and a plunger configured to compress the medical solution container accommodated in the cylinder, the cylinder including an air hole via which an inside thereof and an outside thereof are in communication with each other.

According to a seventeenth aspect of the present invention, the infusion pump system further comprises a deaerating unit provided downstream of the infusion pump 20 and configured to remove an air bubble in the infusion line.

According to an eighteenth aspect of the present invention, the infusion pump system according to any one of the first to seventeenth aspects further comprises a condition input unit into which condition information is input, the condition information being indicative of a condition of the infusion target into which the medical solution is infused; an information storing unit connected to the condition input unit via a communications device and configured to store the condition information input into the condition input unit; and at least one information terminal unit connected to the information storing unit and configured to reference the condition information stored in the information storing unit.

Advantageous Effects of the Invention

With the configuration of the invention of the first aspect, the discharge speed of the infusion pump computed for use in infusing the medical solution at the preset reference infusion speed is corrected using the predefined correction coefficient in accordance with the current discharge speed of the infusion pump and the degree of medical effect in the medical solution.

Accordingly, it is possible to adjust the variation in the discharge speed of the infusion pump in accordance with the degree of medical effects by, for example, assigning the correction coefficient having a small value (e.g., 0.5) to the medical solution that exhibit substantial effect even when administered in a small amount, i.e., the medical solution having higher medical effects, and assigning the correction coefficient having the large value (e.g., 0.9) to the medical solution that only exhibits less substantial effect even when administered in a large amount, i.e., the medical solution having lower medical effects. Further, it is possible to prevent undesirable effects from acting upon the patient due to the change in the infusion speed of the medical solution, and thus ensure improved safety.

With the configuration of the invention of the second aspect, the discharge speed of the infusion pump computed for use in infusing the medical solution within the predefined infusion completion time is corrected using the predefined correction coefficient in accordance with the current discharge speed of the infusion pump and the degree of the medical effects in the medical solution.

Accordingly, it is possible to adjust the variation in the discharge speed of the infusion pump in accordance with the degree of medical effects by, for example, assigning the correction coefficient having a small value (e.g., 0.5) to the medical solution that exhibit substantial effect even when administered in a small amount, i.e., the medical solution having higher medical effects, and assigning the correction coefficient having the large value (e.g., 0.9) to the medical solution that only exhibits less substantial effect even when administered in a large amount, i.e., the medical solution having lower medical effects. Further, it is possible to prevent undesirable effects from acting upon the patient due to the change in the infusion speed of the medical solution, and thus ensure improved safety.

With the configuration of the invention of the third aspect, the predefined safe operation is performed when the discharge speed corrected by the discharge speed correction unit does not fall within the allowable range of the infusion speed for the medical solution computed by the infusion speed range computation unit, the allowable range being computed with reference to the information on the infusion target such as a body weight of the infusion target and the usage and dosage of the medical solution.

Accordingly, it is possible to prevent infusion at an infusion speed that may expose the individual undergoing the infusion al undergoing the infusion to a risk and thus ensure improved safety.

With the configuration of the invention of the fourth aspect, the alarm is triggered as the safe operation. Accordingly, it is possible to alert the medical professionals nearby and prevent infusion at an infusion speed that may expose the individual undergoing the infusion al undergoing the infusion to a risk and thus ensure improved safety.

With the configuration of the invention of the fifth aspect, when the safe operation is entered, discharging of the medical solution by the infusion pump at the corrected discharge speed is prohibited. Accordingly, the current discharge speed of the infusion pump is maintained, so that it is possible to it is possible to prevent infusion at a infusion speed that may expose the individual undergoing the infusion al undergoing the infusion to a risk and thus ensure improved safety.

With the configuration of the invention of the sixth aspect, when the safe operation is entered, discharging (infusion) of the medical solution by the infusion pump is stopped. Accordingly, it is possible to prevent infusion at an infusion speed that may expose the individual undergoing the infusion al undergoing the infusion to a risk and thus ensure improved safety.

With the configuration of the invention of the seventh aspect, the infusion pump includes the piezoelectric pump unit comprising one ore more piezoelectric pumps configured to be operated by the piezoelectric element. Accordingly, the infusion pump becomes compact and light-weight, which leads to reduction in size and weight of the infusion pump system. In addition, the infusion pump of this type is inexpensive and suitable for production in large quantities, which allows the infusion pump 20 to be a disposable product, and thus ensures improved hygienic safety.

With the configuration of the invention of the eighth aspect, the infusion pump includes multiple piezoelectric pump units arranged in parallel with each other; multiple entry tubes each connecting the piezoelectric pumps units to the infusion line, the entry tubes having the bore smaller than that of the infusion line; and the bypass tube configured to connect the entry tubes to each other.

Accordingly, even when any one of the entry tubes is clogged with the solid matter residing in the infusion line, the medical solution is allowed to be drawn in via the other entry tubes and the bypass tube into the piezoelectric pump unit connected to the entry tubes, which allows for uninterrupted discharge operation of the medical solution without malfunctioning of the infusion pump, and thus leads to improved safety.

With the configuration of the invention of the ninth aspect, the infusion pump's piezoelectric pump units previously divided into multiple groups are controlled on a per-group basis using different discharge timings. Accordingly, it is possible to prevent simultaneous discharging of the medical solution by the piezoelectric pump units and prevent the occurrence of the pulsating flow in the medical solution, which contributes to prevention of degradation in the accuracy of flow rate measurement and thus leads to improved safety.

With the configuration of the invention of the tenth aspect, there are provided the medical solution containers each containing corresponding each of the medical solutions and the infusion lines via which the respective medical solutions are drawn out of the medical solution containers, and the infusion pump includes one piezoelectric pump unit and the entry tubes connecting the infusion lines to the piezoelectric pump unit, and the cut-off valves provided in the respective entry tubes and used to block the medical solutions drawn via the infusion line into the piezoelectric pump unit. The cut-off valves are controlled to be opened and closed such that the predefined amounts of the medical solutions are individually drawn into the piezoelectric pump unit.

Accordingly, it is possible to simultaneously infuse the multiple medical solutions using one single infusion pump system through sequentially opening and closing the cut-off valves in a predefined period.

With the configuration of the invention of the eleventh aspect, the cut-off valve is closed after lapse of the predefined negative pressure avoidance time following opening of the next cut-off valve. Accordingly the creation of the negative pressure is prevented in the infusion pump and the infusion set, and it is possible to prevent creation of the air bubbles in the medical solutions, and thus ensure improved safety.

With the configuration of the invention of the twelfth aspect, the control unit is configured to intermittently open and close the at least one of the cut-off valves each provided in corresponding each of the plurality of entry tubes. Accordingly, it can be used in a case where only one medical solution out of the medical solutions needs to be intermittently infused at a predefined interval of, but not limited to, three hours, and it is possible to avoid errors due to manual delivery (e.g., a mistake of not delivering a prescribed medical solution).

With the configuration of the invention of the thirteenth aspect, there is provided the biometric information input unit into which the biometric information is input, the biometric information being measured in the infusion target into which the medical solution is to be infused, and the control unit is configured to open and close the selected one of the cut-off valves on the basis of the biometric information input to the biometric information input unit.

Accordingly, it is possible to selectably deliver the medical solutions in accordance with the biometric information, achieve delivery of the medical solution in accordance with the conditions of the infusion target, and promptly respond to the change in the conditions of the infusion target.

With the configuration of the invention of the fourteenth aspect, there is provided the bypass unit configured to discharge the medical solution via the infusion line with the infusion pump bypassed. Accordingly, it is possible to deliver the medical solution at the necessary infusion speed by virtue of the bypass unit in the event of occurrence of malfunction in the infusion pump and in an emergency situation, and thus ensure improved safety.

With the configuration of the invention of the fifteenth aspect, the infusion pump is provided inside of the medical solution exit portion and inward of the section thereof at which the infusion line is attached to the medical solution container. Accordingly, it is possible to use a conventional infusion line used in conventional infusion sets, as a result of which it is possible to take advantage of existing assets such as the conventional infusion set.

With the configuration of the invention of the sixteenth aspect, there are provided the cylinder accommodating therein the medical solution container made of flexible material; and the plunger configured to compress the medical solution container in the cylinder, the cylinder including the air hole via which the inside thereof and the outside thereof communicates with each other. Accordingly, it is possible to prevent occurrence of the pulsating flow when using the medical solution container comprising the cylinder and the plunger, which contributes to prevention of degradation in the accuracy of flow rate measurement and thus leads to improved safety.

With the configuration of the invention of the seventeenth aspect, there is provided the deaerating unit provided downstream of the infusion pump and configured to remove the air bubble in the infusion line. Accordingly, it is possible to prevent entry of the air bubble into the infusion target, and thus ensure improved safety.

With the configuration of the invention of the eighteenth aspect, there are provided the condition input unit into which the condition information is input indicative of the conditions measured in the infusion target undergoing the infusion of the medical solution; the information storing unit connected to the condition input unit via the communications device and configured to store the condition information input into the condition input unit; and the at least one information terminal unit connected to the information storing unit and configured to reference the condition information stored in the information storing unit. Accordingly, it is possible for the doctor to recognize in realtime the condition of the patient by referencing the condition information at a remote location and using the information terminal unit, and thereby recognize the change in the patient's conditions and make appropriate instructions and treatment in response to the change, which ensures improved safety.

BRIEF DESCRIPTION OF THE DRAWINGS

In the drawings:

FIG. 23 depicts an exemplary configuration of a variation of the infusion pump system depicted in FIG. 21.

Figure 1:
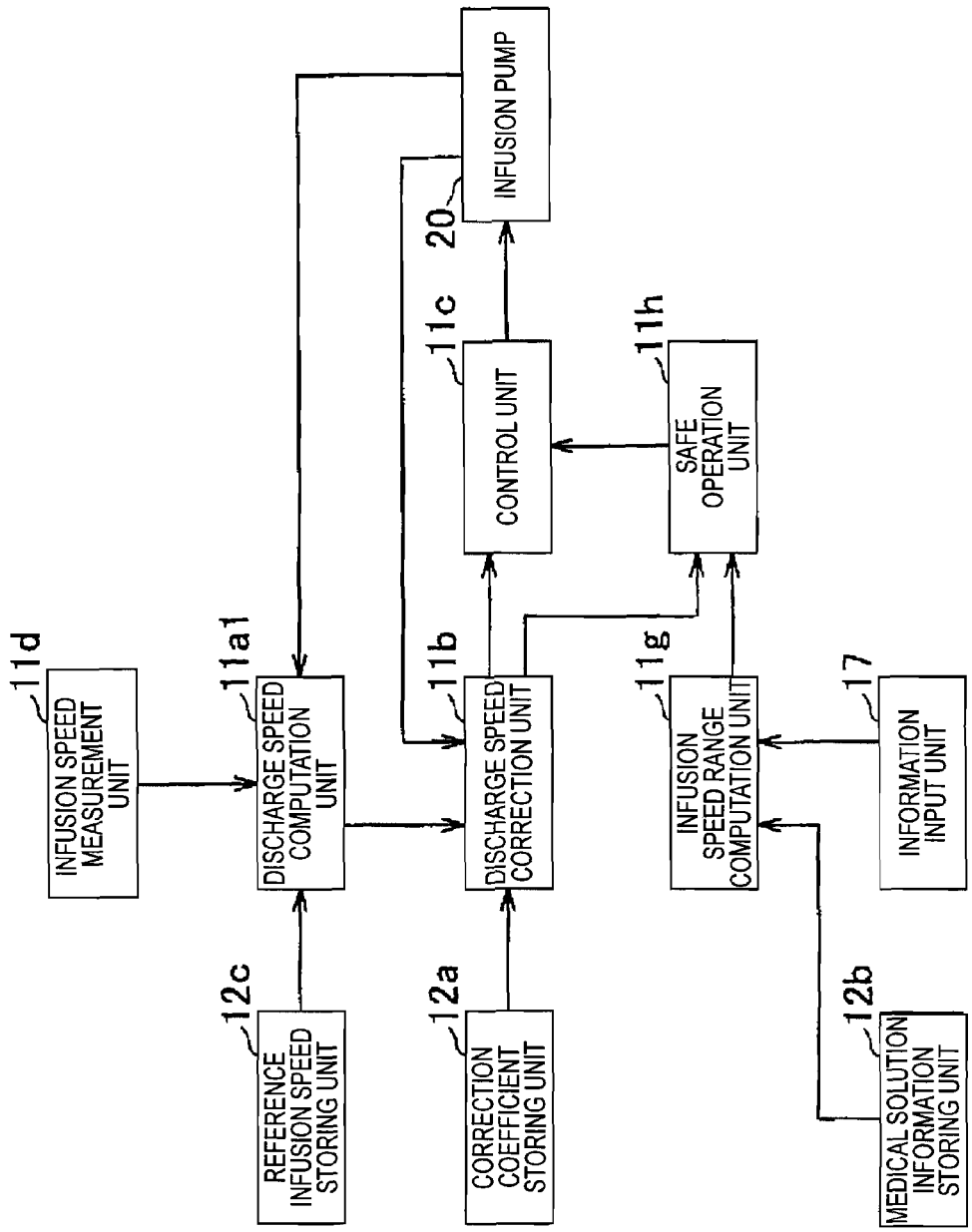
FIG. 1 depicts a basic configuration of the present invention.
Figure 2:
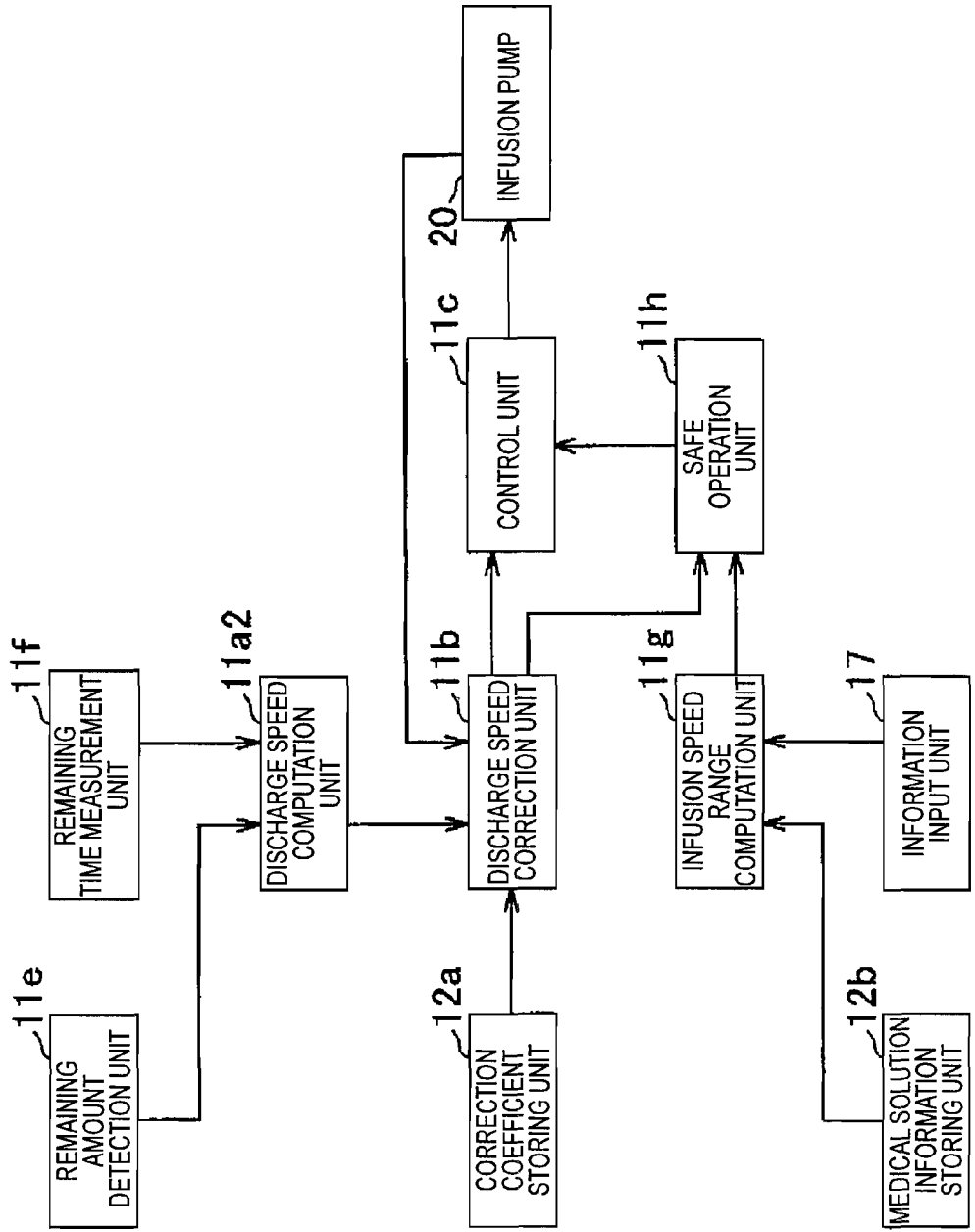
FIG. 2 depicts another basic configuration of the present invention.

REFERENCE SIGNS 1, 2, 3, 4 Infusion pump system
10 Patient terminal
11 CPU (discharge speed computation unit, discharge speed correction unit, control unit, infusion speed measurement unit, remaining amount detection unit, remaining time measurement unit, infusion speed range computation unit, safe operation unit, biometric information input unit, and condition input unit)
12 ROM unit
13 RAM unit (reference infusion speed storing unit)
14 External storage unit (correction coefficient storing unit and medical solution information storing unit)
17 Operation unit (information input unit)
20 Infusion pump
21 Piezoelectric pump unit
22 Piezoelectric pump
23 Entry tube
24 Exit tube
26 Cut-off valve
30 Infusion set
31 Infusion tube
32 Butterfly needle
33 Infusion bottle
40 Infusion bag (medical solution container)
50 Flowmeter
70 Bypass part (bypass unit)
80 Air filter (deaerating unit)

DESCRIPTION OF EXEMPLARY EMBODIMENTS

First Embodiment

An infusion pump system according to a first embodiment of the present invention is described hereinafter with reference to FIGS. 3 to 15. The infusion pump system is configured for automatic infusion or fluid administration at a preset reference infusion speed (which may be referred to as "flow-dependent operation") and automatic infusion within a predefined infusion completion time (which may be referred to as "total-amount-dependent operation").

The flow-dependent operation refers to continuous fluid administration of a preselected medical solution at a constant infusion speed. The infusion speed in the context of this operation may be referred to as the "reference infusion speed." In general, medical solutions have specific maximum dosages (in units of mg/kg/min) per kilogram of a body weight of an infusion target, and delivery of the medical solutions is to be made with an actual dosage thereof not exceeding the maximum dosage.

Infusion of the medical solution is made using a liquid medication comprising a medication and a solvent into which the medication is dissolved.

The infusion speed of the liquid medication, i.e., the reference infusion speed thereof is determined such that the dosage of the medical solution prescribed by a doctor is adhered to. For example, if the dosage of the medical solution which may be prescribed by a doctor is 1 mg/kg/min, then an amount of the medication per 1 cc of the liquid medication (the medical solution concentration) is 40 mg, and the body weight of the infusion target is 80 kg, then the reference infusion speed is 2 cc/min. It should be noted that, throughout the specification, unless indicated otherwise, the medical solution refers to a liquid medication comprising the medication and the solvent in which the medication is dissolved.

The total-amount-dependent operation refers to controlled infusion of a predefined amount of a preselected medical solution to be completed within a predefined period of time. The predefined period of time in this context is referred to as the "infusion completion time." In the case of the total-amount-dependent operation, the infusion speed may vary according to a remaining amount of the medical solution and a remaining time for the infusion completion time.

Figure 3:
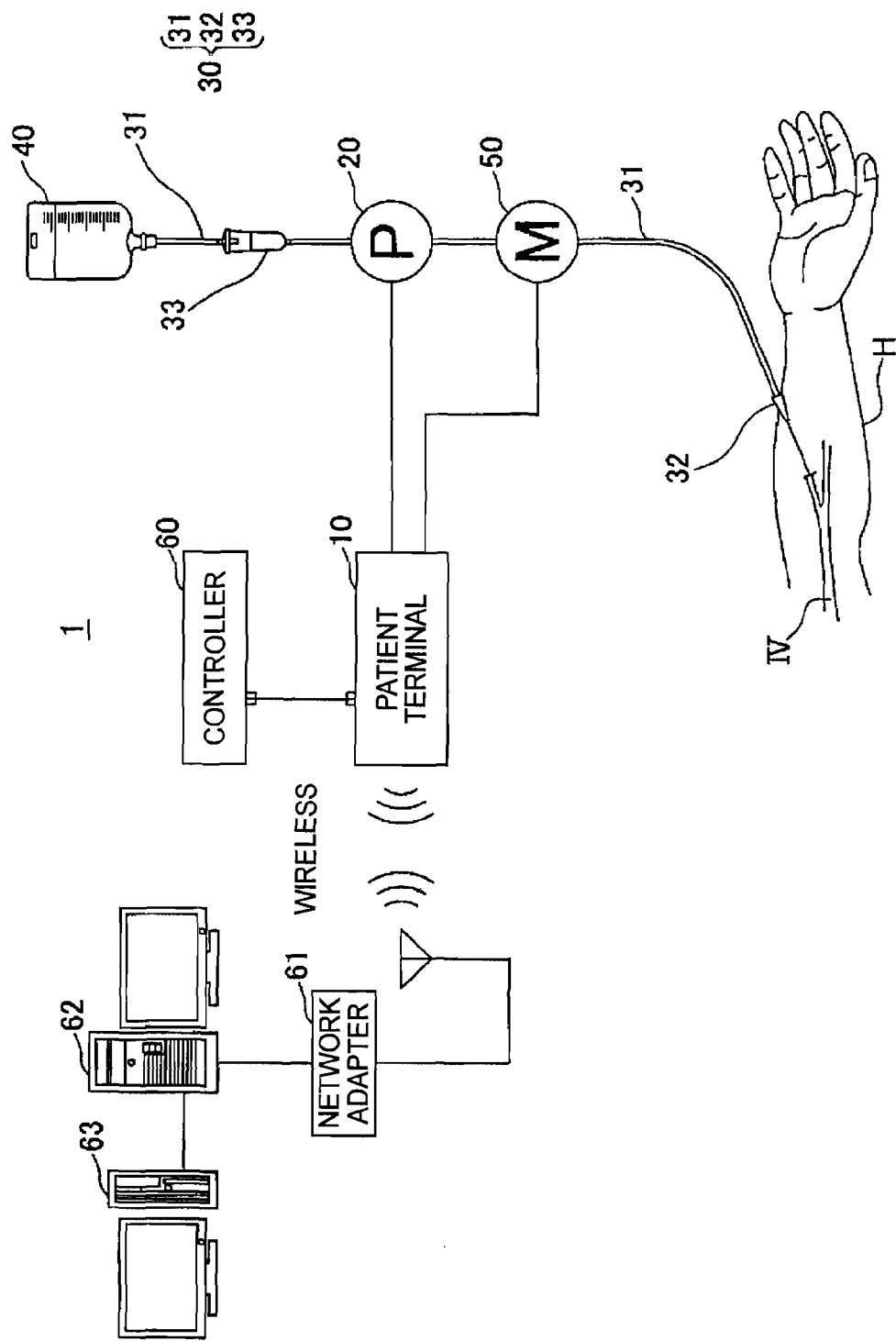
FIG. 3 is a schematic representation of an infusion pump system according to a first embodiment of the present invention.

Referring now to FIG. 3, there is shown an infusion pump system 1 that comprises (a) an infusion bag 40, which may be called a "medical solution bag" and serves as a medical solution container; (b) an infusion set 30 serving as an infusion line; (c) an infusion pump 20; (d) a flowmeter 50; (e) a patient terminal 10; (f) a controller 60; (g) a server computer 62; and (h) an information terminal unit 63.

The infusion bag 40 is a well-known type of a medical solution container containing a medical solution (i.e., a liquid medication comprising a medication and a solvent in which the medication is dissolved), the medical solution being infused into an infusion target H (i.e., a patient). This embodiment contemplates use of one infusion bag 40.

The infusion set 30 comprises (i) a butterfly needle 32 configured to be inserted into a blood vessel IV (a vein) of the patient H; (ii) an infusion tube 31 configured to draw the medical solution out of the infusion bag 40 and draw in the medical solution therethrough to the butterfly needle 32; and (iii) a well-known infusion bottle 33 provided midway in the infusion tube 31 and adapted to count the number of drops during a predefined period for visual measurement of a volume of infusion (which means the infusion speed). It should be noted that, in addition to being inserted into the vein, the butterfly needle 32 may be inserted into a subcutaneous tissue of a human body (i.e., inside of the body) such as artery and muscle.

The infusion pump 20 is a device provided midway in the infusion set 30 and configured to discharge the medical solution contained in the infusion bag 40 into the patient H via the infusion set 30. The infusion pump 20 is connected to the patient terminal 10, which will be described later, so that the discharge speed at which the medical solution is discharged is controlled in accordance with a control signal transmitted from the patient terminal 10.

Figure 4:
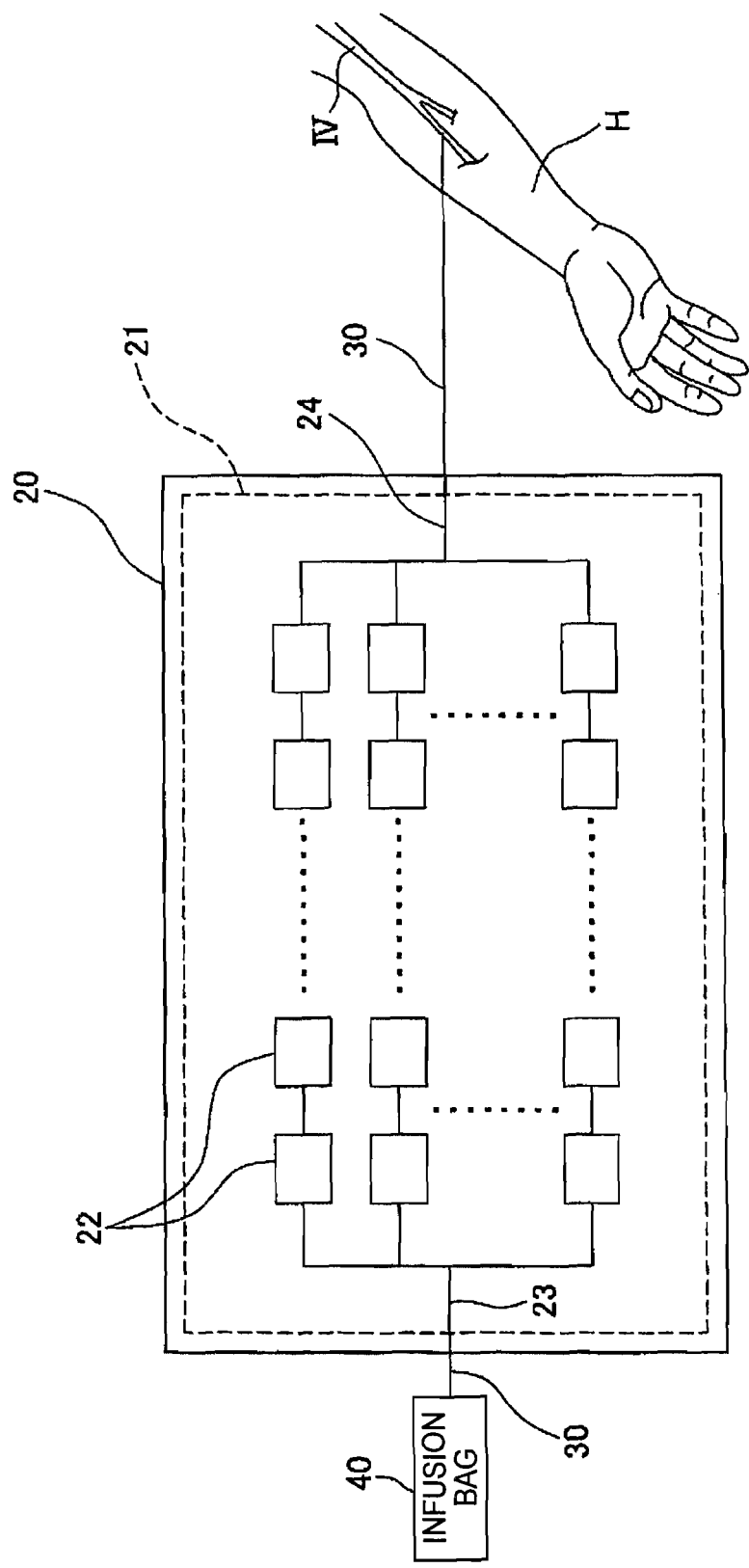
FIG. 4 depicts a configuration of an infusion pump incorporated in the infusion pump system depicted in FIG. 3.

Referring to FIG. 4, the infusion pump 20 includes a piezoelectric pump unit 21 comprising a plurality of piezoelectric pumps 22 driven by a piezoelectric element in series, the piezoelectric pumps 22 connected in series with each other, in parallel with each other, and/or arranged in combination of series and parallel connections. The piezoelectric pump unit 21 may be regarded as a unit constituted by groups of the piezoelectric pumps 22. Even when a plurality of the piezoelectric pump units 21 are provided in series with each other, in parallel with each other, or arranged in combination of the series and parallel connections, the piezoelectric pump units 21 may be regarded as a single piezoelectric pump unit 21 as long as they are controlled by the same control signal or by control signals derived from the same control signal.

The piezoelectric pump unit 21 is connected to an entry tube 23 and a exit tube 24. The entry tube 23 is used to draw the medical solution from the infusion tube 31 into the piezoelectric pump unit 21. The exit tube 24 is used to discharge the medical solution from the piezoelectric pump unit 21.

The infusion set 30 (or more specifically, the infusion tube 31 of the infusion set 30) is connected to both the entry tube 23 and the exit tube 24.

The piezoelectric pump unit 21, the entry tube 23, and the exit tube 24 are made in one piece with each other using well-known Micro-Electro-Mechanical Systems (MEMS) technology based on semiconductor processing techniques.

Figure 5:
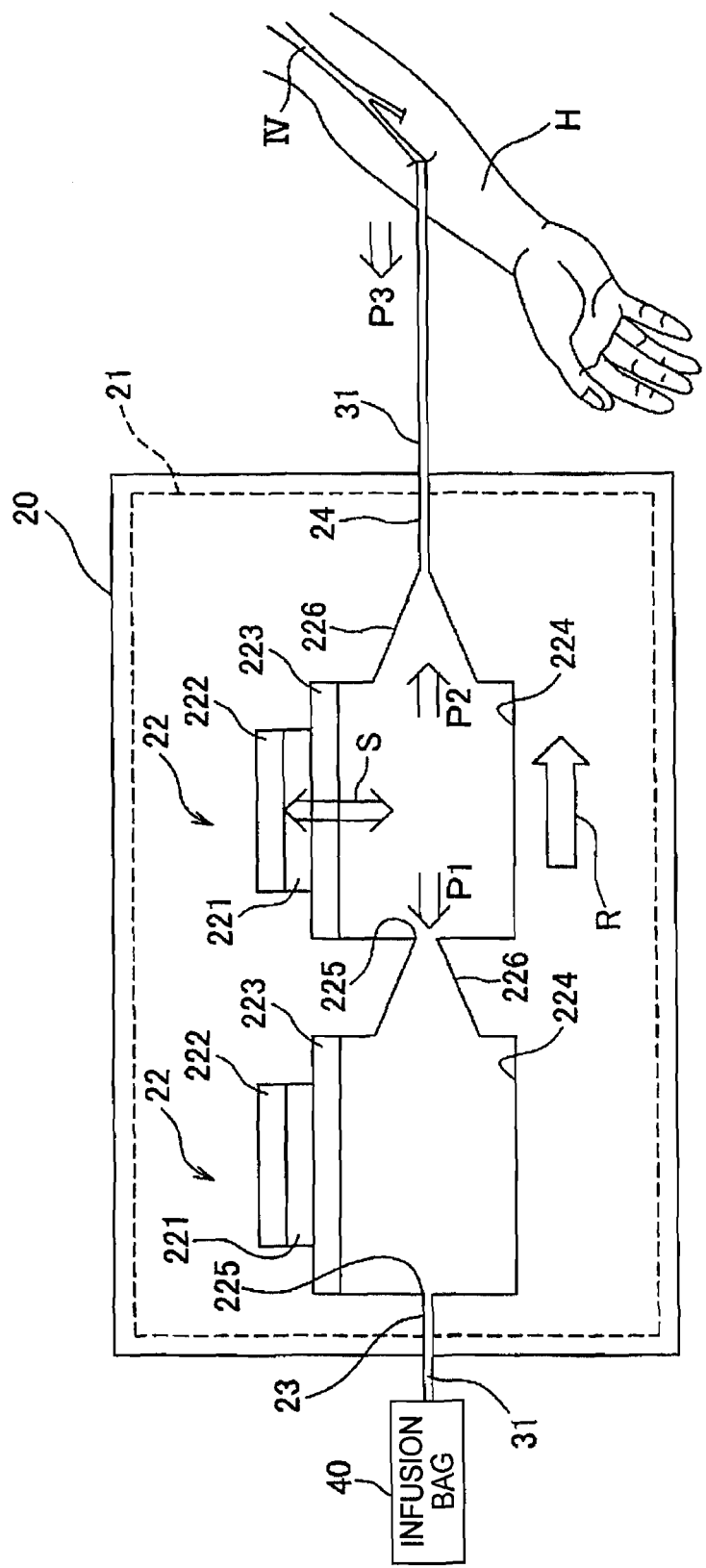
FIG. 5 depicts a configuration of a piezoelectric pump incorporated in the infusion pump depicted in FIG. 4.

Referring to FIG. 5, the piezoelectric pump 22 includes a piezoelectric element 221; an electrode 222 disposed on the piezoelectric element 221 in close contact therewith; a glass plate 223 configured to be oscillated by the piezoelectric element 221 in a direction indicated by an arrow S; a chamber 224 configured to accommodate the medical solution; an inlet hole 225 used to draw the medical solution into the chamber 224; and an outlet hole 226 used to discharge the medical solution from the chamber 224.

The piezoelectric element 221 of the piezoelectric pump 22 is configured to oscillate in accordance with voltage and frequency applied to the electrode 222. The glass plate 223 is configured to oscillate in response to the oscillation of the piezoelectric element 221. The oscillation of the glass plate 223 induces variation in a volume of the chamber 224, so that the medical solution is drawn via the inlet hole 225 into the chamber 224 and the medical solution in the chamber 224 is made to flow from the inlet hole 225 toward the outlet hole 226 (in a direction indicated by an arrow R).

The piezoelectric pump 22 (or the infusion pump 20 having the piezoelectric pump 22) performs discharge operation in accordance with a control signal transmitted from the patient terminal 10. The control signal is used to adjust the voltage and frequency applied to the electrode 222 to cause desired oscillations of the piezoelectric element 221, and thereby control the piezoelectric pump 22 (or the infusion pump 20 having the piezoelectric pump 22) and make the piezoelectric pump 22 discharge the medical solution via the outlet hole 226 at a desired discharge speed.

Although it is contemplated in this embodiment that the infusion pump 20 uses one piezoelectric pump unit 21 and one corresponding entry tube 23, the present invention is not limited to this specific configuration. Given the above specific configuration, however, the entry tube 23 may be clogged with a solid matter residing in the infusion tube 31, i.a., shavings originating from the infusion bag and crystallized components originating from the medical solution. Such clogging may hinder flow of the medical solution and trigger entry of the patient H into a dangerous state.

Figure 6:
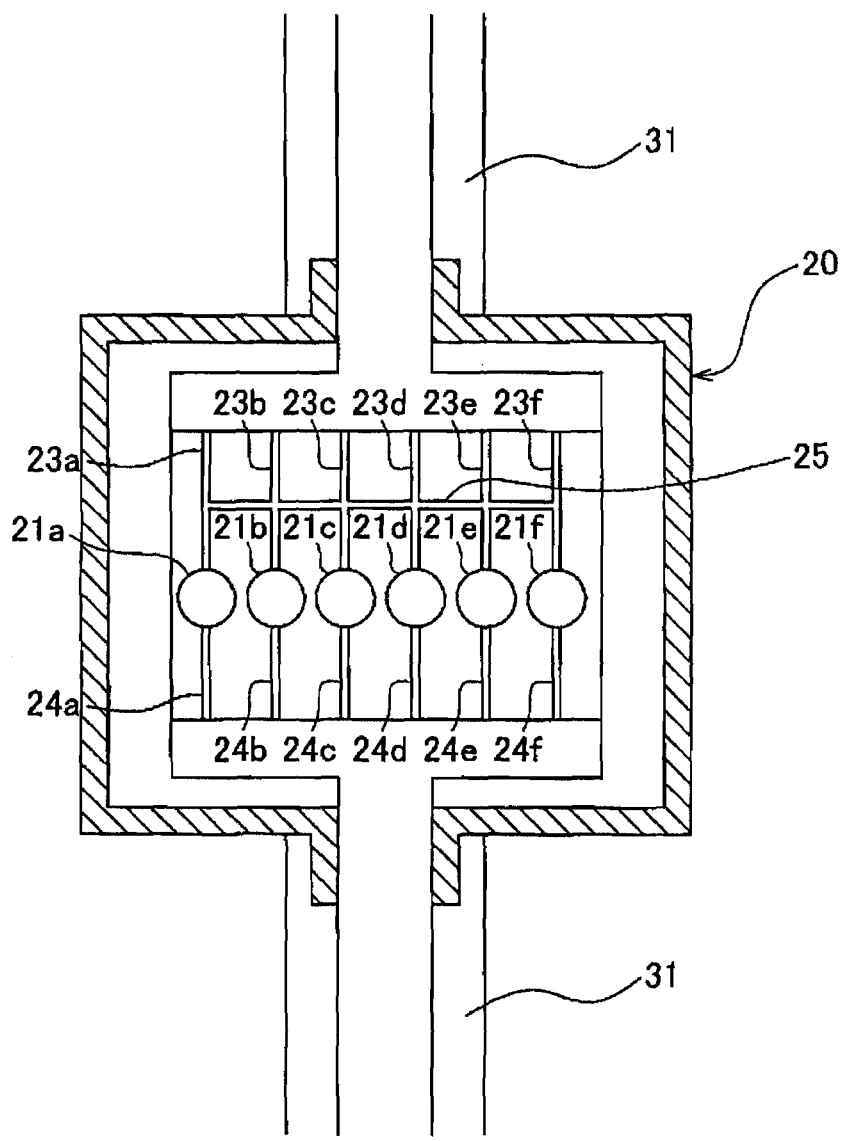
FIG. 6 depicts a variation of the infusion pump of the infusion pump system depicted in FIG. 3.

To address this problem, the infusion pump 20 may include, as shown in FIG. 6, more than one piezoelectric pump unit 21 (i.e., the piezoelectric pump units 21a to 21f) arranged in parallel with each other; more than one entry tube 23 (i.e., entry tubes 23a to 23f) each connecting the piezoelectric pumps units 21 to the infusion tube 31, the entry tubes 23 having a bore smaller than that of the infusion tube 31; and a bypass tube 25 configured to connect the entry tubes 23 to each other. With this alternative configuration of the infusion pump 20, even when any one of the entry tubes 23 is clogged with the solid matter residing in the infusion tube 31, the medical solution is allowed to be drawn in via the other entry tubes 23 and the bypass tube 25 into the piezoelectric pump unit 21 connected to the entry tubes 23, which allows for uninterrupted discharge operation of the medical solution without malfunctioning of the infusion pump 20, and thus leads to improved safety.

In the infusion pump 20 shown in FIG. 6 including the plurality of piezoelectric pump units 21 provided arranged in parallel with each other, it may happen that the amount of medical solution discharged at a time becomes large as the individual piezoelectric pump units 21 simultaneously discharge the medical solution, Further, such a large amount of the medical solution discharged may cause pulsating flow in the medical solution. The pulsating flow may in turn cause inaccuracy in the measurement of the volume of infusion (the infusion speed) by the flowmeter 50, which in turn may cause undesirable effects upon the control of the infusion pump 20.

Figure 7:
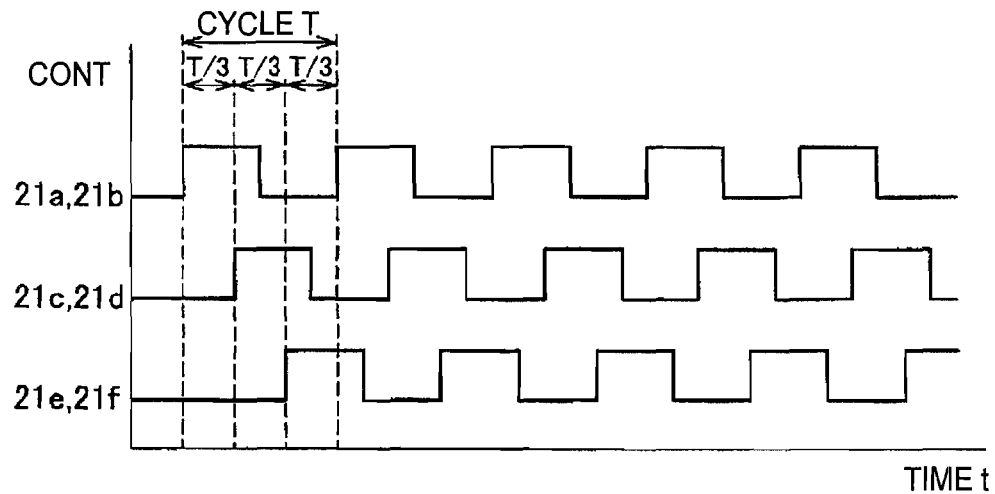
FIG. 7 depicts control signals associated with the infusion pump depicted in FIG. 6.

To address this problem, the amount of the medical solution discharged at one time can be reduced by dividing in advance the piezoelectric pump units 21 of the infusion pump 20 into groups and individually controlling the groups with different discharge timings for prevention of occurrence of the pulsating flow. Specifically, the piezoelectric pump units 21a to 21f shown in FIG. 6 may be divided into three groups of (A) 21a and 21b, (B) 21c and 21d, and (C) 21e and 21f, and the control signals are applied to the groups of piezoelectric pumps 22 as shown in FIG. 7, the control signals being phase-shifted by a third of one cycle with respect to another control signal to assign the different timings on a per-group basis and being individually applied to the groups of the piezoelectric pump 22

The flowmeter 50 is provided midway in the infusion tube 31 and downstream of the infusion pump 20, and configured to measure a flow rate of the medical solution flowing in the infusion tube 31, i.e., the infusion speed of the medical solution. The flowmeter 50 may be constructed by a well-known thermal-diffusion-type flowmeter or an ultrasonic flowmeter. The flowmeter 50 is connected to the patient terminal 10 and configured to periodically transmit information regarding the measured flow rate (i.e., the infusion speed) to the patient terminal 10.

The patient terminal 10 is connected to the infusion pump 20 and the flowmeter 50 and configured to control the discharge speed of the infusion pump 20 such that the medical solution is infused into the patient H at a preset reference infusion speed or within an infusion completion time.

Figure 8:
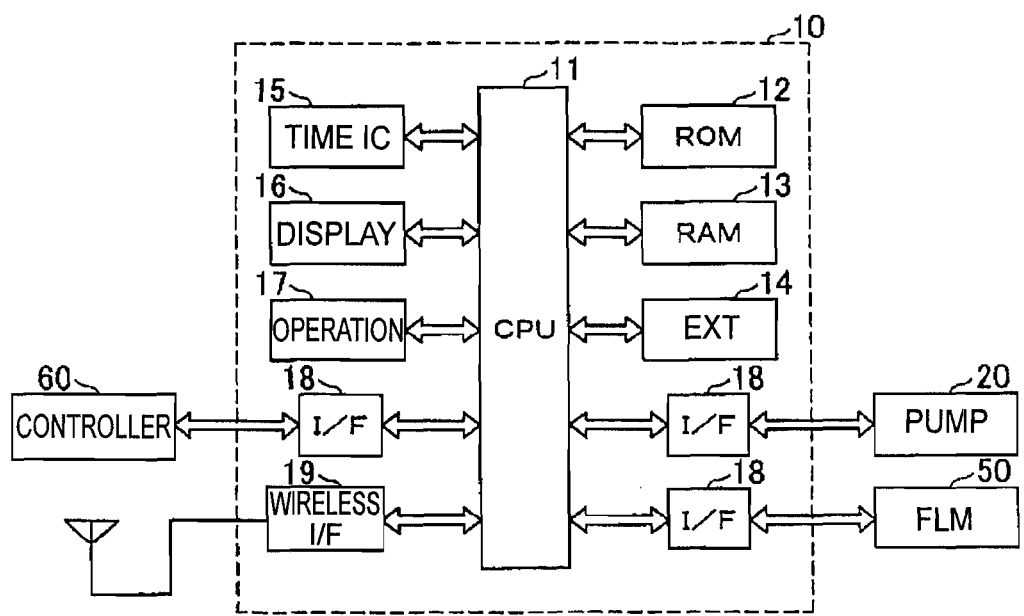
FIG. 8 depicts a configuration of the patient terminal for the infusion pump system depicted in FIG. 3.

Referring to FIG. 8, the patient terminal 10 includes a central processing unit (CPU) 11, a ROM unit 12, a RAM unit 13, an external storage unit 14, a time keeper IC 15, a display unit 16, an operation unit 17, which serves as the information input unit (in the context of the scope of protection), a plurality of external interfaces (I/F) 18, and a wireless interface (wireless I/F) 19.

The CPU 11 controls various operations in the patient terminal 10 (and accordingly the infusion pump system 1) and various processings associated with the control operations in this embodiment in accordance with various control programs stored in the ROM unit 12. The ROM unit 12 stores various information associated with the control programs and the operations of the patient terminal 10. The external storage unit 14 is a mass-storage unit such as a hard disk and a CD-ROM.

The time keeper IC 15 is configured to output time-and-date data to the CPU 11, the time-and-date data being indicative of date and time. The CPU 11 may rely on the time-and-date data to compute the remaining time for the infusion completion time.

The display unit 16 may comprise a liquid crystal display unit and is configured to display various information in response to a request sent from the CPU 11. The display unit 16 may display information including the reference infusion speed, the remaining time for the infusion completion time, the infusion speed of the medical solution for the patient H, and operating states of the infusion pump system 1. In addition, the display unit 16 includes a piezoelectric buzzer configured to trigger an alarm in response to a control signal from the CPU 11.

The operation unit 17 may comprise a touch panel disposed in a superposed manner on the liquid crystal display unit of the display unit 16, various switches, and a keyboard for use in inputting information associated with the patient H and the medical solution. Information that is input to the operation unit 17 may include the reference infusion speed, the infusion completion time, a name of the medical solution for infusion, a total amount of the medical solution for infusion, and a body weight of the patient.

The infusion pump 20, the flowmeter 50, and a controller 60, which will be later described, are connected to the external interfaces I/F 18, respectively, and various devices connected to the external interfaces I/F 18 are configured to transmit and receive the control signals to and from the CPU 11 via the external interfaces I/F 18. Also, these various devices are powered by the patient terminal 10.

A not-shown patient monitoring device is connected to the patient H such that patient's condition of the patient H including body temperature, cardiac rate, and a respiration rate which are measured by the patient monitoring device is input via the external interface (I/F) 18 to the CPU 11 serving as a condition input unit (in the context of the scope of protection).

The wireless interface (wireless I/F) 19 is wireless-connected to the network adapter 61, which serves as the communications device (in the context of the scope of protection), so as to be connected via the network adapter 61 to the server computer 62 serving as the information storing unit on the local area network (LAN) and transmit and receive information on the patient H (for example, the patient's conditions such as the body temperature, the cardiac rate, and the respiration rate) to and from the server computer 62.

The information residing in the server computer 62 is referenced by the information terminal unit 63 connected via the LAIN and installed in a room of a doctor. It should be noted that the communications made by the communications device may be wireless communications or cable communications. This configuration allows realtime recognition of the conditions of the infusion target by the doctor's referencing the patient's condition indicative of the conditions of the patient even when the doctor is in a remote location away from the infusion target, making it possible for the doctor to recognize the change in the conditions of the infusion target and make appropriate instructions in response to the change, and thus lead to ensure improved safety.

The ROM unit 12 stores control programs for the CPU 11 to operate as discharge speed computation units 11a1, 11a2, a discharge speed correction unit 11b, a control unit 11c, an infusion speed measurement unit 11d, a remaining amount detection unit 11e, a remaining time measurement unit 11f, an infusion speed range computation unit 11g, a safe operation unit 11h, a biometric information input unit, and a condition input unit in the context of the scope of protection of the present invention. Further, the CPU 11 functions as these various units through executing the control programs stored in the ROM unit 12. It should be noted that although these units are realized by the CPU 11 of the patient terminal 10, they may be realized by individual computers.

The RAM unit 13 is configured to store information such as the reference infusion speed and/or the infusion completion time the name of the medical solution for infusion, the total amount of the medical solution for infusion, and the body weight of the patient, which are input to the operation unit 17. Specifically, the RAM unit 13 corresponds to the reference infusion speed storing unit in the context of the scope of protection.

The external storage unit 14 may be configured to store correction coefficients used to correct the variation in the discharge speed of any one of the medical solutions, the coefficients being associated with the names of the medical solutions, usage and dosage (maximum dosage, the medical solution concentration in the liquid medication, etc.) of the medical solutions, and the degree of medical effects of the medical solutions. The correction coefficients are associated with these items of information and stored on a per-medical solution basis. It should be noted that the external storage unit 14 corresponds to the correction coefficient storing unit and the medical solution information storing unit in the context of the scope of protection.

The correction coefficient is a coefficient by which the variation in the discharge speed of the infusion pump 20 (i.e., the difference between the previous discharge speed and the new discharge speed) is multiplied. The following describes an example of the correction coefficient.

The degrees of medical effects vary according to types of the medical solutions, some of which may exhibit larger effects with a smaller amount and some of which may only exhibit smaller effects with a larger amount. In view of this, the various types of medical solutions to be delivered to the patients may be classified into three categories. i.e., (a) a medical solution having a higher degree of medical effect (for example, a maximum dosage being less than 1 mg/kg/min), (b) a medical solution having an intermediate degree of medical effect (for example, the dosage being not less than 1 mg/kg/min and not more than 5 mg/kg/min), and (c) a medical solution having a lower degree of medical effect (for example, a maximum dosage being larger than 5 mg/kg/min). The correction coefficient for the medical solution with the higher medical effect is 0.5, the correction coefficient for the medical solution with the intermediate medical effect is 0.7, and the correction coefficient for the medical solution with the smaller medical effect is 0.9. By virtue of such definition of the correction coefficients, it is possible to adjust the variation in the discharge speed in accordance with the degree of the medical effects. It should be noted that the above-described definition is only exemplary, and the correction coefficient and the parameters for classification of the medical solutions may be defined as appropriate.

Next, an exemplary discharge control operation by the CPU 11 of the present invention is described with reference to the flowcharts of FIGS. 9 and 10.

Figure 9:
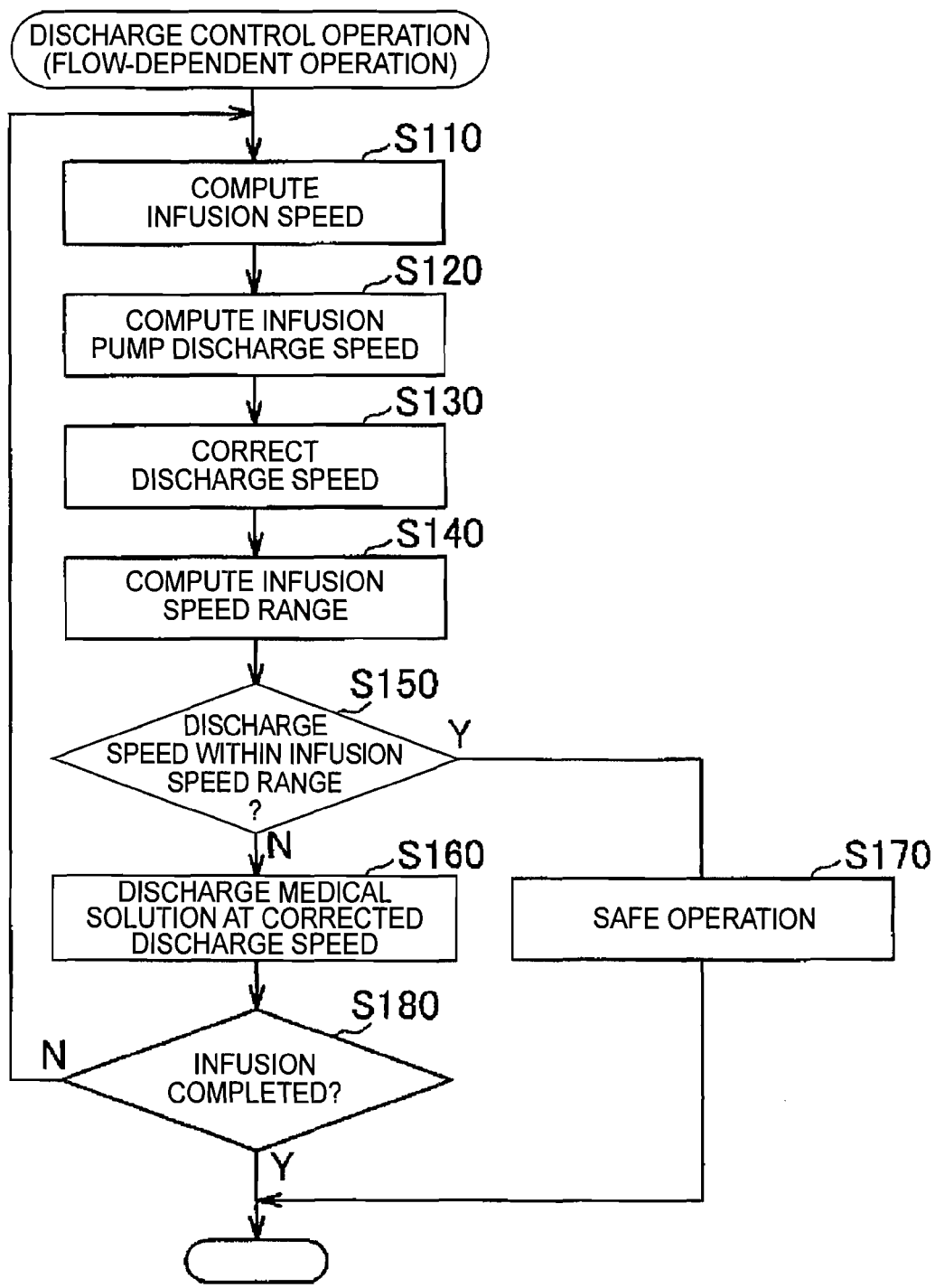
FIG. 9 is a flowchart of the operation of the present invention performed by a central processing unit (CPU) of the patient terminal depicted in FIG. 8.

First, the flow-dependent operation is explained with reference to FIG. 9 showing a flowchart of the flow-dependent operation.

When the patient terminal 10 is activated, the infusion pump 20 and the flowmeter 50 are also activated. After the activation of the infusion pump 20 and the flowmeter 50, the CPU 11 performs predefined initialization operation and waits for the information regarding the name of the medical solution contained in the infusion bag 40, body weight of the patient, the reference infusion speed, and the total amount of the medical solution to be input to the operation unit 17. When the information regarding the name of the medical solution contained in the infusion bag 40, body weight of the patient, the reference infusion speed, and the total amount of the medical solution has been input to the infusion operation unit 17, the information is stored in the RAM unit 13 and the discharge control operation (flow-dependent operation) illustrated in FIG. 9 is started.

The CPU 11 computes the infusion speed of the medical solution flowing through the infusion tube 31 with reference to the information regarding the flow rate transmitted from the flowmeter 50 (S110).

Next, the CPU 11 computes the discharge speed of the infusion pump 20 for the infusion of the medical solution to be made at the reference infusion speed by multiplying (a) the current discharge speed of the infusion pump 20 stored in the RAM unit 13 (at an initial state, the reference infusion speed)

by (b) the reference infusion speed stored in the RAM unit 13 divided by the infusion speed computed in the previous step (S120).

Further, the variation in the discharge speed, i.e., the difference between the current discharge speed of the infusion pump 20 obtained in the step S110 and the computed discharge speed of the infusion-pump 20 obtained in the step S120, is computed, and the correction coefficient is read out, the correction coefficient being associated with the name of the medical solution stored in the RAM unit 13 and being stored in the external storage unit 14. The variation in the discharge speed is multiplied by the correction coefficient. The resulting value is added to the current discharge speed. Thus, the computed discharge speed is corrected (S130).

Restated, in the step S120, the discharge speed of the infusion pump 20 for infusion of the medical solution at the reference infusion speed is expressed by the following equation:

$$V1 = Vp \times (Vs/Vr) \quad \text{(Eqn. 1)}$$

where V1 is the discharge speed V1 of the infusion pump 20 for infusion of the medical solution at the reference infusion speed; Vr is the computed infusion speed of the medical solution; Vp is the current discharge speed of the infusion pump; and Vr is the reference infusion speed.

In the step S130, the corrected discharge speed V2 of the infusion pump 20 is expressed by the following equation:

$$V2 = Vp + (V1 - Vp) \times E \quad \text{(Eqn. 2)}$$

where V2 is the corrected discharge speed of the infusion pump 20; V1 is the discharge speed of the infusion pump 20 obtained in the step S120, and E is the correction coefficient associated with the name of the medical solution and stored in the external storage unit.

After that, an allowable infusion speed range for the medical solution is computed with reference to the usage and dosage of the medical solution associated with the medical solution name stored in the RAM unit 13 and stored in the external storage unit 14 and with reference to the body weight of the patient stored in the RAM unit 13 (S140). For example, with regard to the usage and dosage of the medical solution, if the maximum dosage is specified to be not less than 1 mg/kg/min and not more than 5 mg/kg/min, and if the body weight of the patient is 60 kg, then the allowable infusion speed range will be the dosage of the medical solution not less than 60 mg/min and up to 300 mg/min.

Subsequently, judgment is made regarding whether or not the corrected discharge speed of the infusion pump 20 falls within the allowable infusion speed range. If the discharge speed of the infusion pump is not within the infusion speed range (Y in the step S150), then the alarm is triggered by the piezoelectric buzzer of the display unit 16, and the discharge operation of the infusion pump 20 is stopped (i.e., safe operation, S170), the operation is terminated. If the discharge speed of the infusion pump is within the infusion speed range (N in the step S150), then a control signal is transmitted to the infusion pump 20 to make the infusion pump 20 discharge the medical solution at the corrected discharge speed, and the corrected discharge speed is stored in the RAM unit 13 to be regarded thereafter as the current discharge speed.

After that, if an accumulated value of the volume of infusion obtained by integration of the computed infusion speed is less than the total amount of the medical solution for infusion stored in the RAM unit 13, then the above operation is continued and repeatedly performed at the predefined period (N in the step S180). If the total amount of the medical solution for infusion is reached, then discharge operation of the infusion pump 20 is stopped and the operation is completed.

It should be noted that the step S110 corresponds to the infusion speed measurement unit in the context of the scope of protection; the step S120 corresponds to the discharge speed computation unit in the context of the scope of protection; the step S130 corresponds to the discharge speed correction unit in the context of the scope of protection; the step S140 corresponds to the infusion speed range computation unit in the context of the scope of protection; the step S160 corresponds to the control unit in the context of the scope of protection; and the step S170 corresponds to the safe operation unit in the context of the scope of protection.

Figure 10:
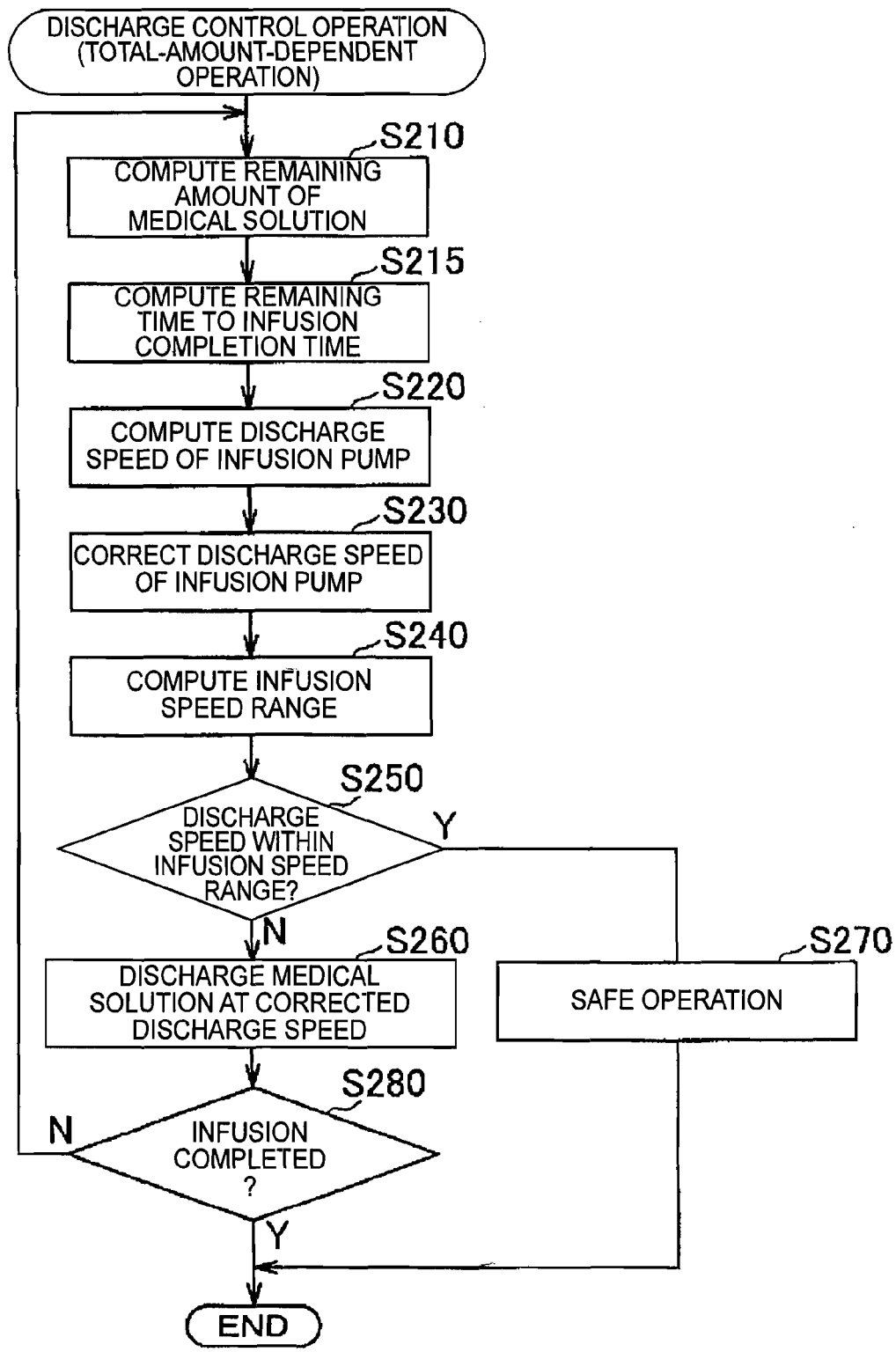
FIG. 10 is another flowchart of the operation of the present invention performed by the CPU of the patient terminal depicted in FIG. 8.

The total-amount-dependent operation is hereinafter explained with reference to FIG. 10 showing a flowchart of the total-amount-dependent operation.

When the patient terminal 10 is activated, the infusion pump 20 and the flowmeter 50 are activated. After the activation of the infusion pump 20 and the flowmeter 50, the CPU 11 performs a predefined initialization operation and waits for waits for the information regarding the name of the medical solution contained in the infusion bag 40, body weight of the patient, the reference infusion speed, and the total amount of the medical solution to be input to the operation unit 17. When the information regarding the name of the medical solution contained in the infusion bag 40, the body weight of the patient, the infusion completion time, and the total amount of the medical solution for infusion is input to the operation unit 17, then the information is stored in the RAM unit 13 and the discharge control operation (i.e., the total-amount-dependent operation) illustrated in FIG. 10 is started.

The CPU 11 computes the volume of infusion with reference to the information regarding the flow rate transmitted form the flowmeter 50, and subtracts the computed volume of infusion from the total amount of the medical solution contained in the RAM unit 13, and thus computes the remaining amount of the medical solution (S210). Further, with reference to the time-and-date data output by the time keeper IC 15, the remaining time for the infusion completion time is computed or measured (S215).

Subsequently, the computed remaining amount of the medical solution obtained in the previous step is divided by the computed remaining time for the infusion completion time obtained in the previous step, and thus the discharge speed of the infusion pump 20 for infusion of the medical solution within the infusion completion time is computed (S220).

Further, the variation in the discharge speed, i.e., the difference between the current discharge speed (in an initial state, a predefined initial discharge speed) of the infusion pump 20 stored in the RAM unit 13 and the computed discharge speed, is computed. The correction coefficient associated with the medical solution name stored in the RAM unit 13 and stored in the external storage unit 14 is read out. The computed discharge speed is multiplied by the read correction coefficient. The resulting value is added to the current discharge speed, and thus the computed discharge speed is corrected (S230).

Restated, in the step S220, the discharge speed V3 of the infusion pump 20 for infusion of the medical solution within the infusion completion time is computed by the following equation:

$$V3 = W/Tr \quad \text{(Eqn. 3)}$$

where V3 is the discharge speed of the infusion pump 20 for infusion of the medical solution within the infusion completion time; W is the computed remaining amount of the medical solution; and Tr is the computed remaining time for the infusion completion time.

In the step 230, the corrected discharge speed V4 of the infusion pump 20 is obtained by the following equation:

$$V4 = Vp + (V2 - Vp) \times E \quad \text{(Eqn. 4)}$$

where V4 is the corrected discharge speed of the infusion pump 20; V2 is the discharge speed computed in the step S220; and E is the correction coefficient associated with the medical solution name and stored in the external storage unit 14.

After that, an allowable infusion speed range for the medical solution is computed with reference to the usage and dosage of the medical solution associated with the name of the medical solution stored in the RAM unit 13 and stored in the external storage unit 14 and with reference to the body weight of the patient stored in the RAM unit 13 (S240).

Subsequently, judgment is made regarding whether or not the above corrected discharge speed of the infusion pump 20 falls within the allowable infusion speed range. If the discharge speed of the infusion pump is not within the infusion speed range (Y in the step S250), the alarm is triggered by the piezoelectric buzzer of the display unit 16 and the discharge operation of the infusion pump 20 is stopped (i.e., safe operation, S270), and the operation is terminated. If the discharge speed of the infusion pump is within the infusion speed range (N in the step S250), then the control signal is transmitted to the infusion pump 20 to make the infusion pump 20 discharge the medical solution at the corrected discharge speed, and the corrected discharge speed is stored in the RAM unit 13 to be regarded thereafter as the current discharge speed.

After that, if the remaining amount of the medical solution is not equal to zero, then the above operation is repeatedly performed for a predefined period (N in the step S280). If the remaining amount of the medical solution is equal to zero, then the discharge operation of the infusion pump 20 is stopped and the operation is completed.

It should be noted that the above-described the step S210 corresponds to the remaining amount detection unit in the context of the scope of protection; the step S215 corresponds to the remaining time measurement unit in the context of the scope of protection; the step S220 corresponds to the discharge speed computation unit in the context of the scope of protection; the step S230 corresponds to the discharge speed correction unit in the context of the scope of protection; the step S240 corresponds to the infusion speed range computation unit in the context of the scope of protection; the step S260 corresponds to the control unit in the context of the scope of protection; and the step S270 corresponds to the safe operation unit in the context of the scope of protection.

It should also be noted that the safe operation is not limited to the above-described one where the alarm is triggered to stop the discharge operation of the infusion pump 20. As the safe operation, any one of the following items alone or in combination may be supported: (i) triggering an alarm; (ii) stopping the discharge operation of the infusion pump 20; and (iii) maintaining the current discharge speed of the infusion pump 20. By virtue of the safe operation of this type, it is possible to prevent infusion at an infusion speed that may expose the individual undergoing the infusion to a risk and thus lead to improved safety.

Also, in the above description, the volume of infusion and the remaining amount of the medical solution are computed on the basis of the information regarding the flow rate transmitted from the flowmeter 50. However, the embodiment is not limited to this configuration. For example, the volume of infusion and the remaining amount of the medical solution may be computed on the basis of measurement of a weight of the infusion bag 40.

The controller 60 includes a well-known computer, a display unit such as a liquid crystal display unit configured to display various information, an operation unit such as a touch panel disposed in a superposed manner on the liquid crystal display unit, a switch, and a keyboard for inputting various information, and a communications device connected to the patient terminal 10 and adapted for use in wireless or cable communications with the patient terminal 10.

The controller 60 is a device separated from the patient terminal 10 to be operated by doctors, nurses, and other medical professionals for various operations controlling the patient terminal 10 such as changing the parameters in the patient terminal 10 including the infusion completion time and the reference infusion speed specified. This is due to the fact that the patient terminal 10 is usually placed adjacent to the patient's bed. If the parameters can be changed by the patient terminal 10, the patient getting sick and tired of the infusion might change the infusion completion time and the reference infusion speed to complete the infusion more quickly.

To preclude such an incident, the parameters specified in the patient terminal 10 are only allowed to be modified via the controller 60. Also, all of the operations available on the patient terminal 10 are also possible via the controller 60.

In this manner, according to the present invention, the computed discharge speed of the infusion pump 20 for infusion of the medical solution at the preset reference infusion speed is corrected by the predefined correction coefficient in accordance with the current discharge speed of the infusion pump 20 and the degree of the medical effects of the medical solution. Accordingly, it is possible to adjust the variation in the discharge speed of the infusion pump, allowing prevention of adverse effects upon the patient due to the change in the infusion speed of the medical solution, and thus ensuring improved safety.

Also, the discharge speed of the infusion pump 20 computed for infusion of the medical solution within the predefined infusion completion time is corrected by the predefined correction coefficient in response to the current discharge speed of the infusion pump 20 and the degree of the medical effects of the medical solution. Accordingly, it is possible to adjust the variation in the discharge speed of the infusion pump in response to the degree of the medical effects, and thereby prevent adverse effects upon the patient due to the change in the infusion speed of the medical solution, and thus ensure improved safety.

Further, if the corrected discharge speed of the infusion pump does not fall within the range of the allowable infusion speed for the medical solution computed on the basis of the information on the infusion target such as the body weight and the usage and dosage of the medical solution, then the predefined safe operation is performed. Accordingly, it is possible to prevent infusion at an infusion speed that may expose the individual undergoing the infusion to a risk and thus ensure further improved safety.

Also, as the safe operation, the alarm is triggered to alert the medical professionals. Accordingly, it is possible to prevent infusion at an infusion speed that may expose the individual undergoing the infusion to the risk and thus further ensure improved safety.

Further, as the safe operation, the discharging (infusion) of the medical solution by the infusion pump is stopped, and accordingly it is possible to prevent infusion at an infusion speed that may expose the individual undergoing the infusion to the risks and thus ensure improved safety.

Also, the infusion pump 20 includes the piezoelectric pump unit 21 comprising one ore more piezoelectric pump 22 configured to be operated by the piezoelectric element. Accordingly, the infusion pump 20 becomes compact and light-weight, which leads to reduction in size and weight of the infusion pump system 1. In addition, the infusion pump 20 of this type is inexpensive and suitable for production in large quantities, which allows the infusion pump 20 to be a disposable product, and thus ensures improved hygienic safety.

In the meantime, doctors and nurses are usually so quite hectic with their work that it is almost impossible for them to constantly attend patients at bed side. Heretofore, in the case of the state-of-the-art infusion pump systems, when an abnormal condition of a patient has been detected, the infusion pump system triggers an alarm to bring it to the attention of the doctors and/or the nurses so that a nurse who is near the site recognizes the condition of the patient and he or she reports the doctor about the situation in order that the doctor can implement suitable measures.

The down side to it, however, is that this conventional process takes time. If the patient has a serious symptom, taking a long time to respond to it might lead to further aggravation in acuteness of his or her symptom.

In this context, the present invention includes (a) the patient terminal 10 connected to the patient monitoring device measuring the condition of the patient, the measured patient's condition being input to the terminal 10; (b) the server computer 62, which serves as the information storing unit (in the context of the scope of protection), connected to the patient terminal 10 via communications device and configured to store the patient's condition input to the patient terminal 10; and (c) one or more information terminal unit 63 connected by LAN to the server computer 62 and used to reference the patient's condition stored in the server computer 62.

Accordingly, it is possible for the doctor to recognize in realtime the condition of the patient by referencing the patient's condition at a remote location (for example, a doctor's room) and using the information terminal unit 63, and thereby recognize the change in the patient's conditions and make appropriate instructions and treatment in response to the change, which ensures improved safety.

It should be noted that the infusion pump system of the above-described embodiment employs the infusion pump 20 that includes the piezoelectric pump unit 21 comprising one or more piezoelectric pumps 22 driven by the piezoelectric element for infusion. However, for example, in the field such as emergency response that involves human life, a large amount of medical solution may have to be given in a short period of time in response to patient's conditions. Nevertheless, in the above-described infusion pump 20, due to the capacity of the piezoelectric element, there is a limit on the maximum infusion speed, failing to meet such requirements.

Figure 11:
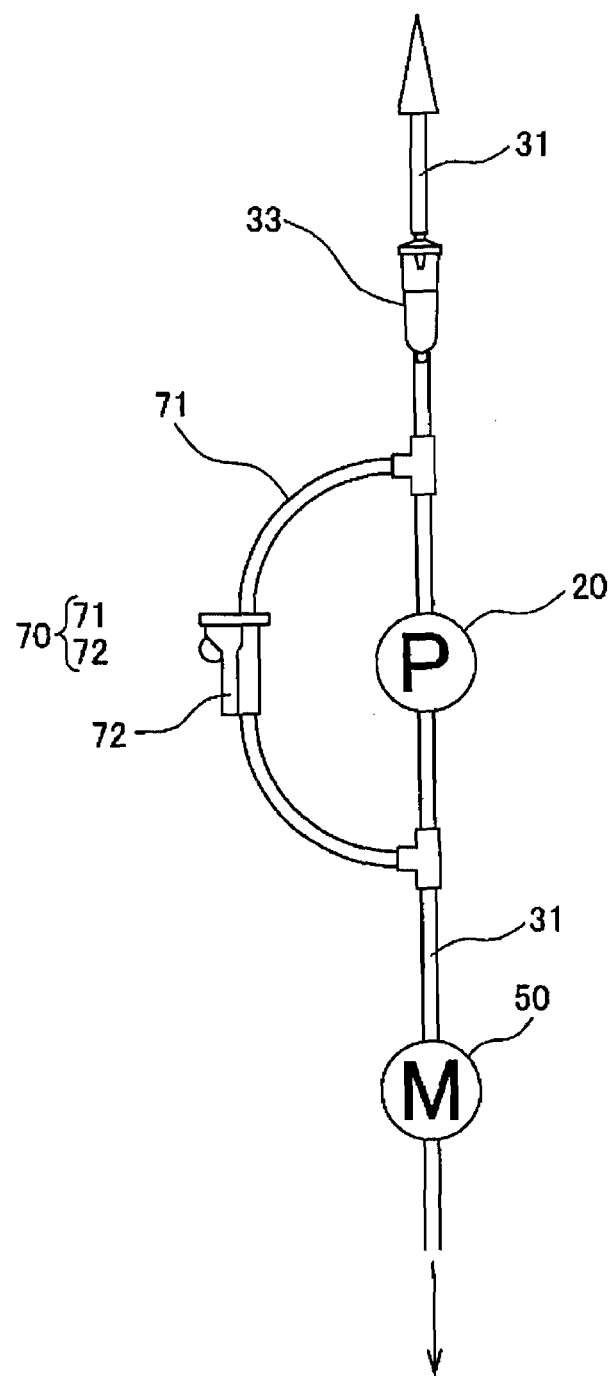
FIG. 11 depicts a configuration of the infusion pump system depicted in FIG. 3 that further includes a bypass unit.
Figure 12:
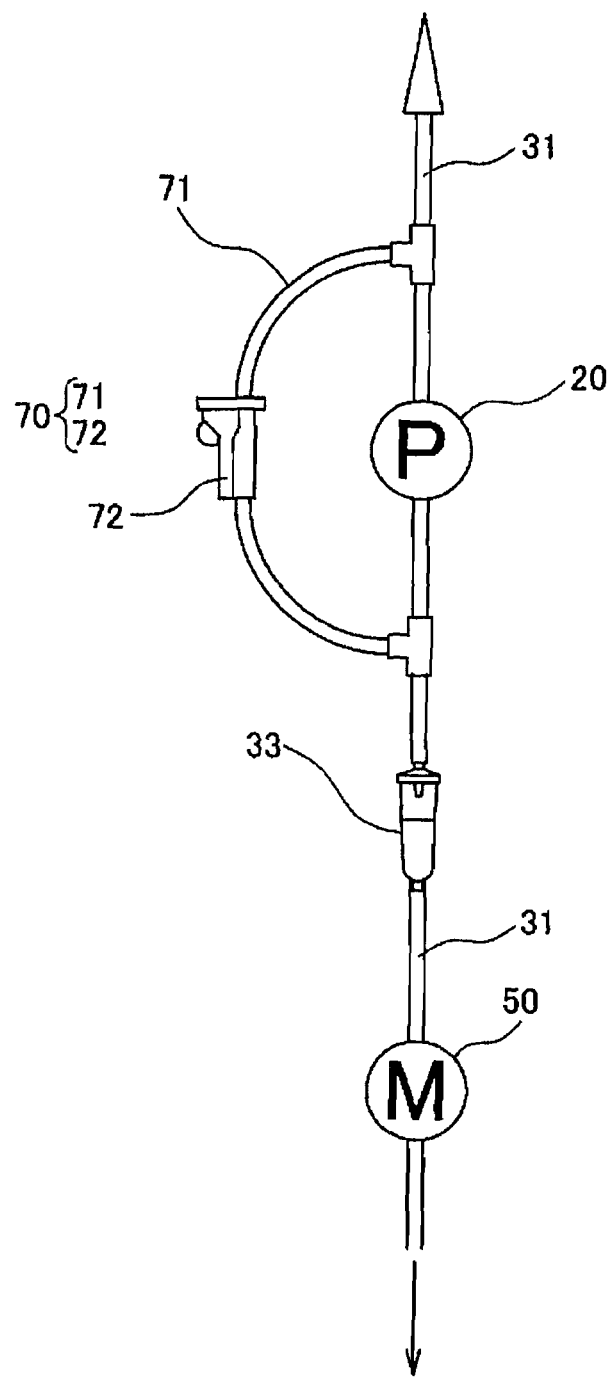
FIG. 12 depicts another configuration of the infusion pump system depicted in FIG. 3 that further includes the bypass unit.

To address this problem, there may be provided a bypass part 70 serving as the bypass unit (in the context of the scope of protection), as shown in FIGS. 11 and 12, which comprises (a) a bypass tube 71 branching from the infusion tube 31 and connected again to the infusion tube 31 with the infusion pump 20 bypassed; and (b) a well-known clamp 72 provided midway in the bypass tube 71 and configured to adjust the flow rate of the medical solution flowing through the bypass tube 71.

In normal use, the clamp 72 is closed preventing entry of the medical solution into the bypass tube 71. In an emergency situation where a large amount of the medical solution has to be delivered in a short period of time, the clamp 72 is opened so that the medical solution is allowed to flow in the bypass tube 71. In this manner, the infusion pump 20 is bypassed by virtue of the bypass part 70 allowing the medical solution to be infused at a required infusion speed, and resulting in improved safety. It should be noted that although the position of the infusion bottle 33 in FIG. 11 is not the same as that shown in FIG. 12, any position may be selected, as long as the flowmeter 50 is provided downstream of the bypass part 70 in order to measure the amount of the medical solution that has been infused.

In the meantime, in the above-described embodiment, as a result of the operation of the infusion pump 20, a negative pressure is created in the chamber 224 of the piezoelectric pump 22 and fine air bubbles may be created in the medical solution. The fine air bubbles may be brought into the patient along with the medical solution.

Figure 13:
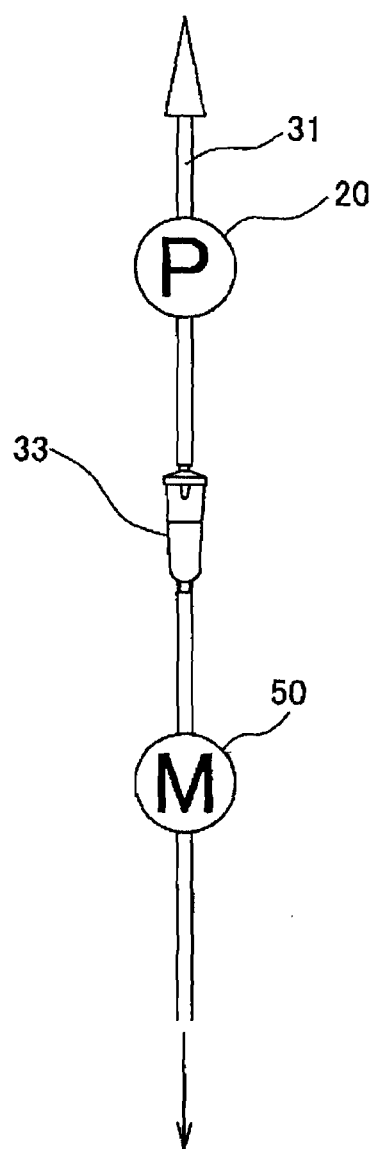
FIG. 13 depicts an exemplary configuration of the infusion pump system depicted in FIG. 3 that further includes an infusion bottle serving as the deaerating unit.
Figure 14:
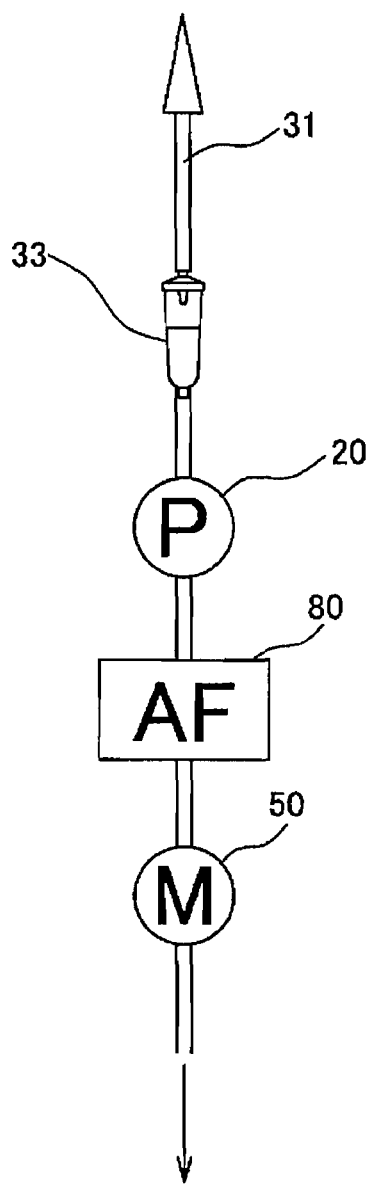
FIG. 14 depicts a configuration of the infusion pump system depicted in FIG. 3 that further includes an air filter serving as the deaerating unit.

To address this, there may be provided a deaerating unit arranged downstream of the infusion pump and yet upstream of the flowmeter to remove the fine air bubbles. Referring to FIG. 13, there is shown a configuration including an infusion bottle 33 which also serves as the deaerating unit. Referring to FIG. 14, there is shown a configuration including a well-known air filter 80 (for example, Toray's infusion filter TI) that serves as the deaerating unit.

Figure 15:
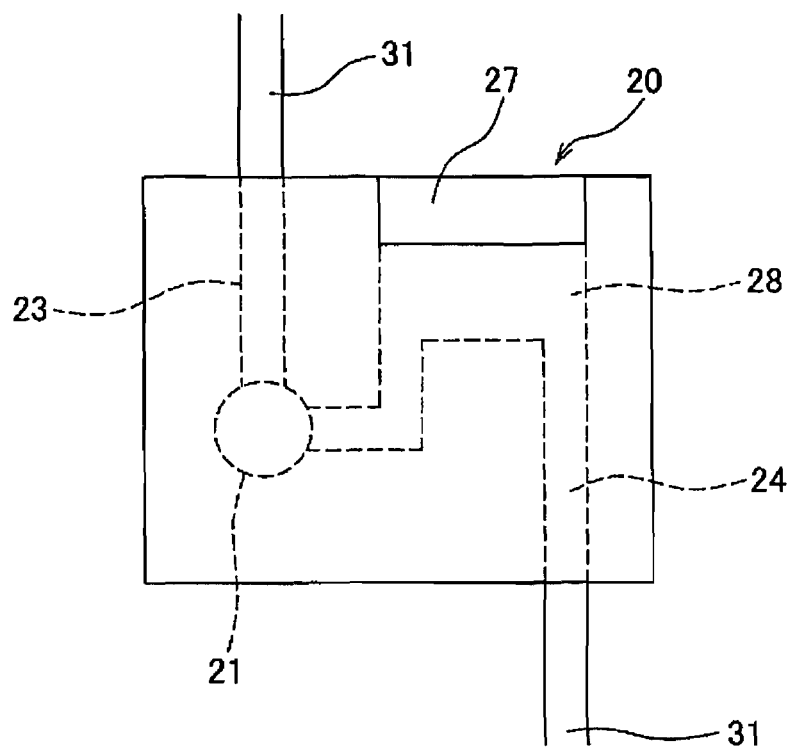
FIG. 15 depicts an exemplary configuration of the infusion pump system depicted in FIG. 3 that further includes a deaerating unit provided in the infusion pump.

Also, FIG. 15 illustrates a configuration where the deaerating unit is provided inside of the infusion pump 20. The infusion pump 20 includes (a) an air trap chamber 28 provided midway in the exit tube 24 and upward of an outlet of the exit tube 24; and (b) a hydrophobic filter 27 above the air trap chamber 28 and configured to prevent passage of the medical solution therethrough while at the same time letting the air pass therethrough.

Since the hydrophobic filter 27 also has to prevent passage of bacteria in the air therethrough, the hydrophobic filter 27 has a fine mesh in order of not more than 1 μm.

By virtue of the deaerating unit of this type, the fine air bubbles in the medical solution are removed, so that entry of the fine air bubble into the patient can be effectively prevented, which ensures improved safety.

Second Embodiment

An infusion pump system according to a second embodiment of the present invention is described hereinafter with reference to FIGS. 16 to 20.

Figure 16:
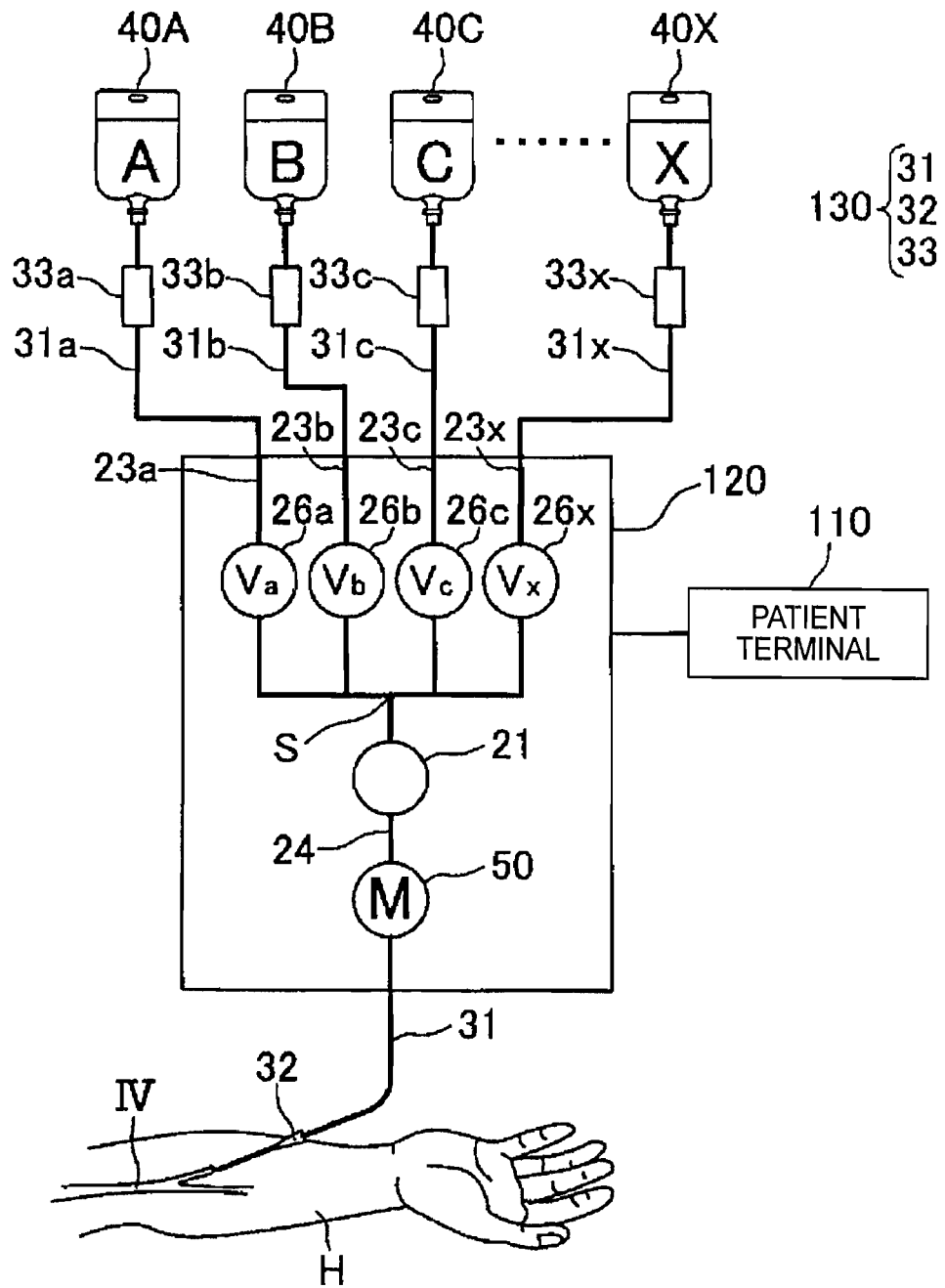
FIG. 16 depicts an exemplary configuration of an infusion pump system according to a second embodiment of the present invention.

Referring to FIG. 16, the infusion pump system 2 comprises a plurality of infusion bags 40 (40A to 40X) as the medical solution container (in the context of the scope of protection); an infusion set 130 as the infusion line; an infusion pump 120; and a patient terminal 110.

The infusion bag 40 is a well-known medical solution container configured to contain the medical solution for infusion to an infusion target H (i.e., a patient). This embodiment relies on multiple infusion bags 40. The infusion set 130 includes a butterfly needle 32 sized and dimensioned to be inserted into a blood vessel (vein) IV of the patient H; an infusion tube 31 that draws the medical solution from the infusion bag 40 and guides the medical solution therethrough into the butterfly needle 32; and a well-known infusion bottle 33 provided midway in the infusion tube 31 for visual measurement of the volume of infusion (the infusion speed) by counting the number of drops in a predetermined period. The infusion set 130 includes a plurality of infusion tubes 31 (31a to 31x) provided between the infusion bag 40 and the infusion pump. It should be noted that butterfly needle 32 may, in addition to being inserted in the vein, be inserted into a subcutaneous tissue of a human body (i.e., inside of the body) such as an artery and a muscle for use in infusion.

The infusion pump 120 is provided midway in the infusion set 130 and configured to discharge the medical solutions contained in the infusion bags 40 via the infusion set 130 into the patient H. The infusion pump 120 is connected to the patient terminal 110 and configured to select the medical solutions for infusion in accordance with the control signal sent from the patient terminal 110 and control the discharge speed of the medical solution.

The infusion pump 120 includes one piezoelectric pump unit 21 which is equivalent to the infusion pump 20 of the first embodiment. Connected to the piezoelectric pump unit 21 are: a plurality of entry tubes 23 (23a to 23x) configured to draw in the medical solution from the plurality of infusion tubes 31 and guide it to the piezoelectric pump unit 21; and an exit tube 24 through which the medical solution is discharged from the piezoelectric pump unit 21. An infusion set 130 (or more specifically the infusion tube 31) is connected to the entry tubes 23 and the exit tube 24.

The entry tubes 23 each includes corresponding each of cut-off valves 26 (26a to 26x) configured to be opened and closed to control the flow of the medical solution in the entry tube 23. The opening and closing timings of the cut-off valves 26 are controlled by the control signal transmitted from the patient terminal 110. The flowmeter 50 is configured to measure the flow rate of the medical solution flowing in the exit tube 24. The piezoelectric pump unit 21, the entry tubes 23, the exit tube 24, the cut-off valves 26, and the flowmeter 50 are made in one piece with each other using well-known Micro-Electro-Mechanical Systems (MEMS) technology based on semiconductor processing techniques.

It should be noted that this embodiment relies on the MEMS techniques and forms the cut-off valves 26 in one piece with the piezoelectric pump unit 21. However, the present invention is not limited to this specific configuration. The cut-off valves 26 may be provided in the form of an externally-attached element, and for example, upstream of the infusion pump 20 in the context of the first embodiment. In this case, the combination of the infusion pump 20 and the set of the cut-off valves 26 in the form of the externally attached elements may be regarded as a single infusion pump.

The patient terminal 110 has the same configuration and functionality as those of the patient terminal 10 of the first embodiment illustrated in FIG. 8. The patient terminal 110 is connected via external interfaces I/F 18 to the infusion pump 120 to receive the information on the infusion speed of the medical solution from the flowmeter 50 of the infusion pump 120 and transmit the control signal for controlling the discharge speed of the piezoelectric pump unit 21. It should be noted that the modes of control of the discharge speed of the piezoelectric pump unit 21 is the same as those of the first embodiment, explanation of which is omitted.

Further, the patient terminal 110 controls the cut-off valves 26 so that they are sequentially opened and closed in response to the information on the dosages of the medical solutions each stored in the external storage unit 14. Specifically, the patient terminal 110 makes the infusion tubes 31 connect to the piezoelectric pump unit 21 in a time-division manner (time-sharing manner) so as to infuse the plurality of the medical solutions substantially simultaneously into the patient H.

Figure 17:
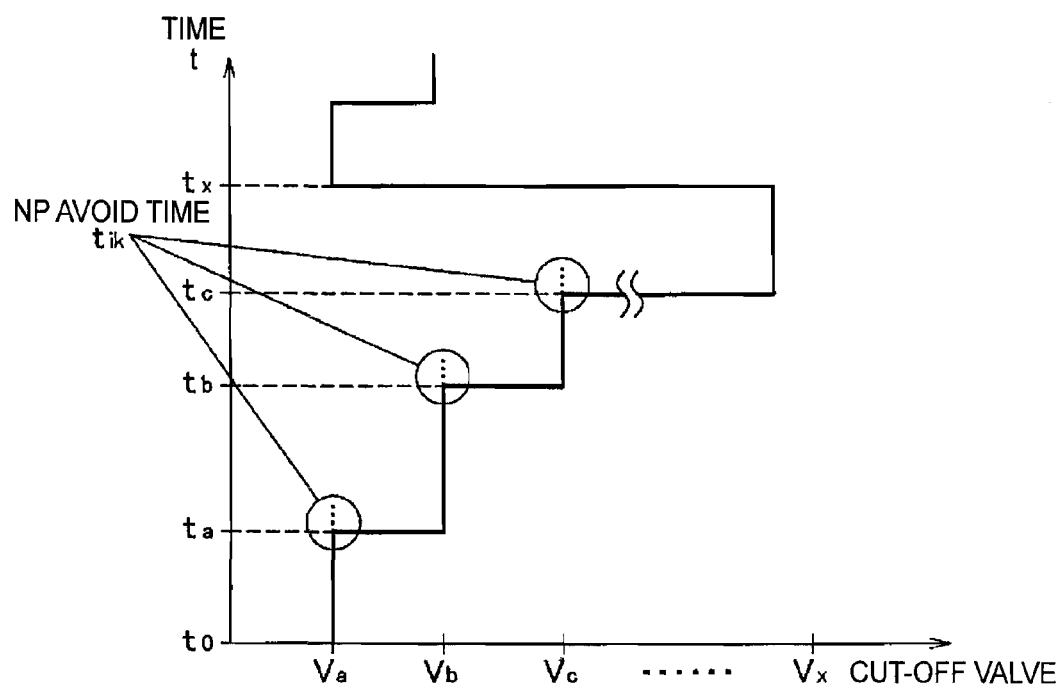
FIG. 17 depicts methodology of controlling a cut-off valve provided in an infusion pump of the infusion pump system depicted in FIG. 16.

FIG. 17 illustrates an example of how the cut-off valves 26 are controlled. The patient terminal 110 in its initial state closes all of the cut-off valves 26. When the infusion is started (t0), the cut-off valve 26a is opened and the medical solution contained in the infusion bag 40A is drawn via the entry tube 23a into the piezoelectric pump unit 21. After that, when the valve-open time ta for the cut-off valve 26a has elapsed, the cut-off valve 26b is opened. After that, when a predefined negative pressure avoidance time tik has elapsed, the cut-off valve 26a is closed. In the same manner, the next cut-off valve 26 is opened in response to lapse of the valve-open time for each of the cut-off valves 26, thereafter in response to a lapse of a predefined negative pressure avoidance time tik, the previously-opened cut-off valve 26 is closed, and this operation is sequentially repeated. The valve-open time for each of the cut-off valves 26 is determined in accordance with the dosage of the medical solution whose flow is controlled by each of the cut-off valves.

In the above infusion pump 120, fine air bubbles may be created in the medical solution when the closing operation of the previous cut-off valve 26 is done simultaneously with the opening operation of the next cut-off valve 26. The process of creation of the air bubbles may be illustrated as follows with reference to FIG. 16. When closing of the cut-off valve 26a occurs simultaneously with opening of the cut-off valve 26b, a venture effect is produced due to the flow of the entry tube 23b caused by opening of the cut-off valve 26b in the tube section extending from the cut-off valve 26a to the confluence point S of the entry tubes 23, so that the medical solution remaining in the entry tube 23a is sucked into the section of the entry tube 23 at and following the confluence point S, and as a result, the entry tube 23a is placed under a negative pressure, causing the creation of the fine air bubbles. Also, in order to prevent the creation of the fine air bubbles, it is necessary to replenish the medical solution continuously for a predefined period for avoidance of the negative pressure in the entry tube 23 in the event of opening the cut-off valve 26. Accordingly there is provided a negative pressure avoidance time to ensure that the closing of the cut-off valve 26a and the opening of the cut-off valve 26b do not take place simultaneously.

In this manner, according to the present invention, there are provided (a) the infusion bags 40 each containing corresponding each of the plurality of the medical solutions; and (b), the infusion set 30 (i.e., plurality of infusion tubes 31) through which the medical solutions are drawn out of each of the infusion bags 40. The infusion pump 120 includes (i) one piezoelectric pump unit 21; (ii) the entry tubes 23 connecting the piezoelectric pump unit 21 to the infusion tubes 31; and (iii) the cut-off valves 26 provided in corresponding each of the entry tubes 23 and configured to control the flow of the medical solution drawn via the infusion tube 31 into the piezoelectric pump unit 21. The cut-off valves 26 are controlled to be opened and closed such that the predefined amount of the medical solution is drawn into the piezoelectric pump unit 21 via each of the entry tubes 23. Accordingly it is possible to simultaneously infuse the medical solutions using one single infusion pump system through sequentially opening and closing the cut-off valves in a predefined period.

Also, the cut-off valve 26 is closed after lapse of the predefined negative pressure avoidance time following opening of the next cut-off valve 26. Accordingly the creation of the negative pressure is prevented in the infusion pump 120 and the infusion set 130, and it is possible to prevent creation of the air bubbles in the medical solutions, and thus ensure improved safety.

It should be noted that although, in the above-described embodiment, the medical solutions are infused simultaneously in accordance with the time-division methodology, the present invention is not limited to this specific configuration. For example, when the medical solutions are to be infused, the present invention may be used in a situation where only one medical solution out of the medical solutions needs to be intermittently infused at a predefined interval of, but not limited to, three hours.

Figure 18:
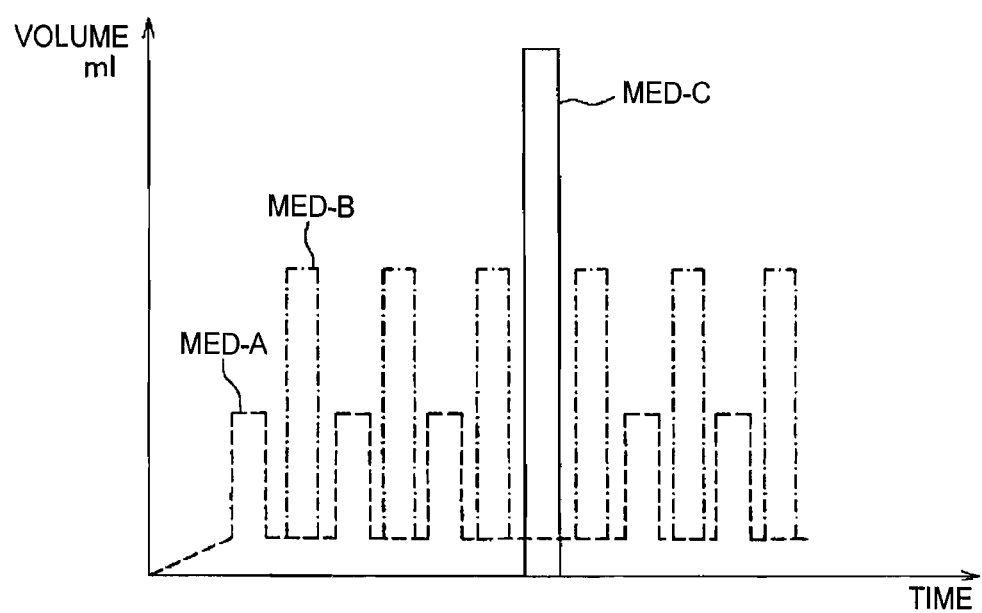
FIG. 18 depicts methodology of controlling the infusion pump system depicted in FIG. 16 to intermittently deliver the medical solution.

FIG. 18 describes an example of how the intermittent infusion of this kind can be controlled. There are provided the medical solution A and the medical solution B, and the cut-off valves 26 are controlled such that a predefined amount of the medical solution A and the medical solution B are repeatedly infused alternately. Meanwhile, with regard to the medical solution C, a predefined amount thereof is infused for each predefined period and by a predefined portion. In this manner, it is possible to avoid errors due to manual delivery (e.g., a mistake of not delivering a prescribed medical solution).

Figure 19:
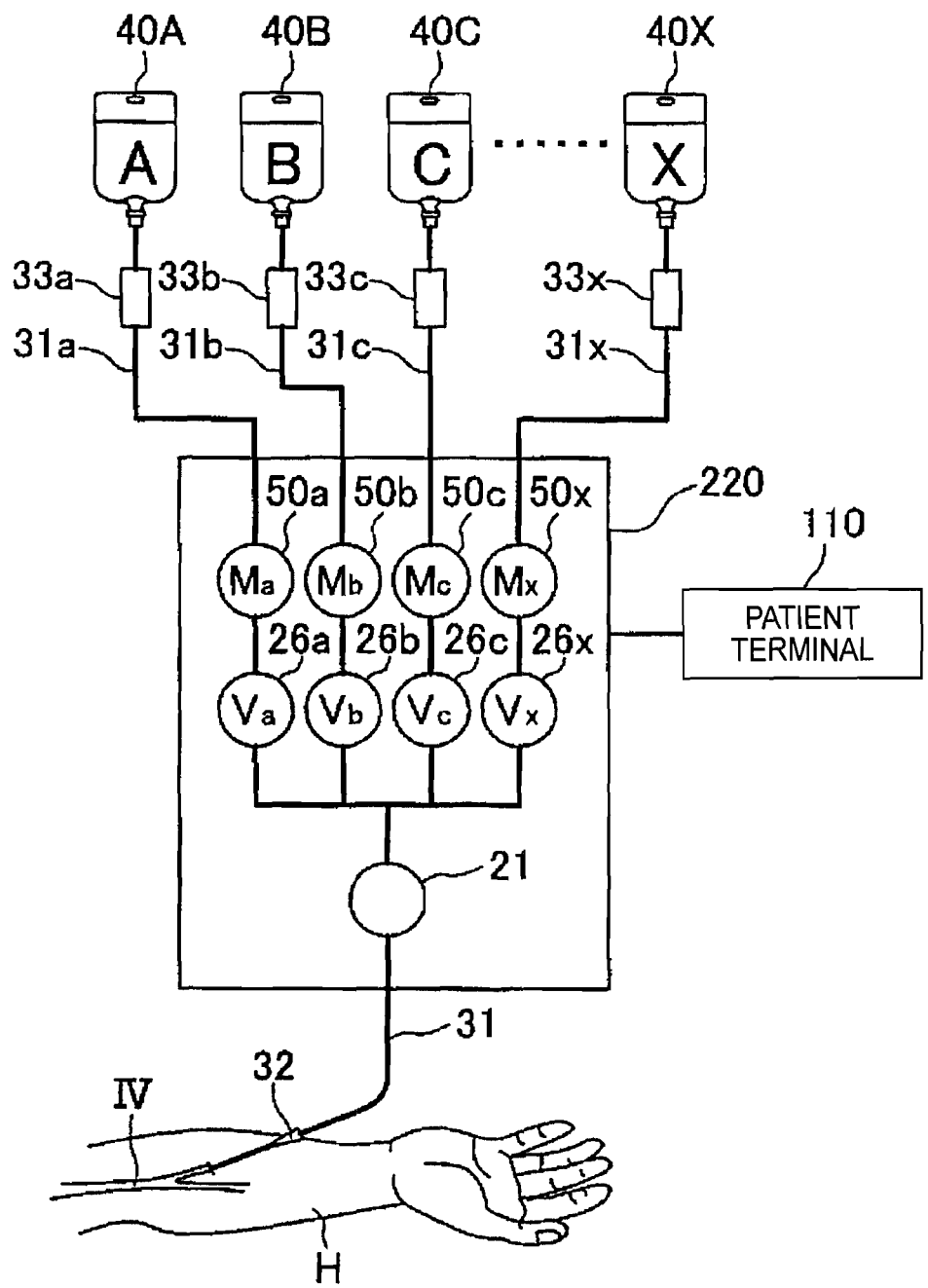
FIG. 19 depicts an exemplary configuration of a variation of the infusion pump of the infusion pump system depicted in FIG. 16.

Also, in the configuration of the above-described embodiment, the flowmeter 50 in the infusion pump 120 is provided downstream of the piezoelectric pump unit 21 for measurement of the total volume of infusion (the infusion speed) of the medical solutions. However, the present invention is not limited to this specific configuration. For example, as illustrated in FIG. 19, the infusion pump 220 may comprise the plurality of the entry tubes 23 that each include corresponding each of the plurality of flowmeters 50 (50a to 50x). In this manner, it is possible to measure the volume of infusion on a per-medical solution basis, and thus facilitate more accurate infusion.

Also, in the above-described embodiment, the biometric information J measured associated with the patient H is input to the patient terminal 110, and the patient terminal 110 may select one of the medical solutions for infusion with reference to the content of the biometric information J. An example of the infusion pump system with this configuration is illustrated in FIG. 20.

Figure 20:
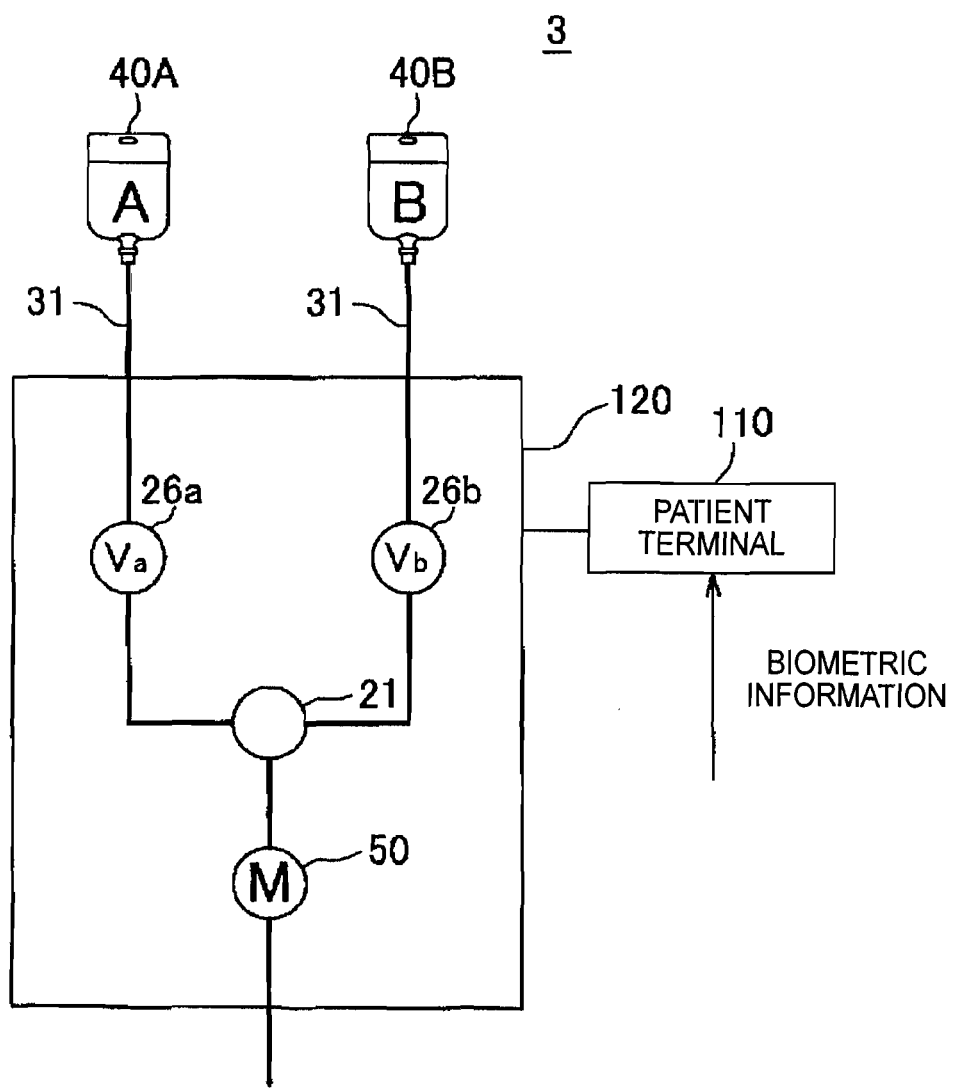
FIG. 20 depicts an exemplary configuration of the infusion pump system depicted in FIG. 16 associated with controlling the infusion pump on the basis of patient's biometric information.

Referring to FIG. 20 illustrating the configuration of an infusion pump system 3, an infusion bag 40A and an infusion bag 40B are connected to an infusion pump 120 via an infusion set 130 (more specifically, an infusion tube 31), The infusion bag 40A contains an antihypertensive (e.g., beta-adrenergic blocking agent) for reduction of blood pressure of the patient H. The infusion bag 40B contains a vasopressor (e.g., catecholamine) for increase in the blood pressure of the patient H. A not-shown blood-pressure measurement unit may be connected to the patient H so that information on the blood pressure of the patient H measured by the blood-pressure measurement unit (i.e., the biometric information) is input to the CPU 11 via the external interfaces I/F 18 provided in the patient terminal 110, the CPU 11 serving as the biometric information input unit (in the context of scope of protection).

Further, when a systolic blood pressure of the patient H exceeds a predefined upper limit (for example, 150 mmHg), the infusion pump 120 is controlled so as to deliver the antihypertensive (i.e., the cut-off valve 26a is opened). When a diastolic blood pressure of the patient H falls below a predefined lower limit (for example, 40 mmHg), the infusion pump 120 is controlled so as to deliver the vasopressor is infused (i.e., the cut-off valve 26b is opened). Also, when the blood pressure of the patient H is more than the lower limit or less than the upper limit, control is performed so that neither of the medical solutions is infused (i.e., both the cut-off valve 26a and the cut-off valve 26b are closed). In this manner, delivery of the medical solution can be automatically performed in accordance with the conditions of the patient (infusion target), allowing prompt response to changes in the patient's conditions.

It should be noted that the above-described embodiment may also comprise the bypass unit and the deaerating unit of the first embodiment.

Third Embodiment

An infusion pump system according to a third embodiment of the present invention is described hereinafter with reference to FIGS. 21 to 23.

Figure 21:
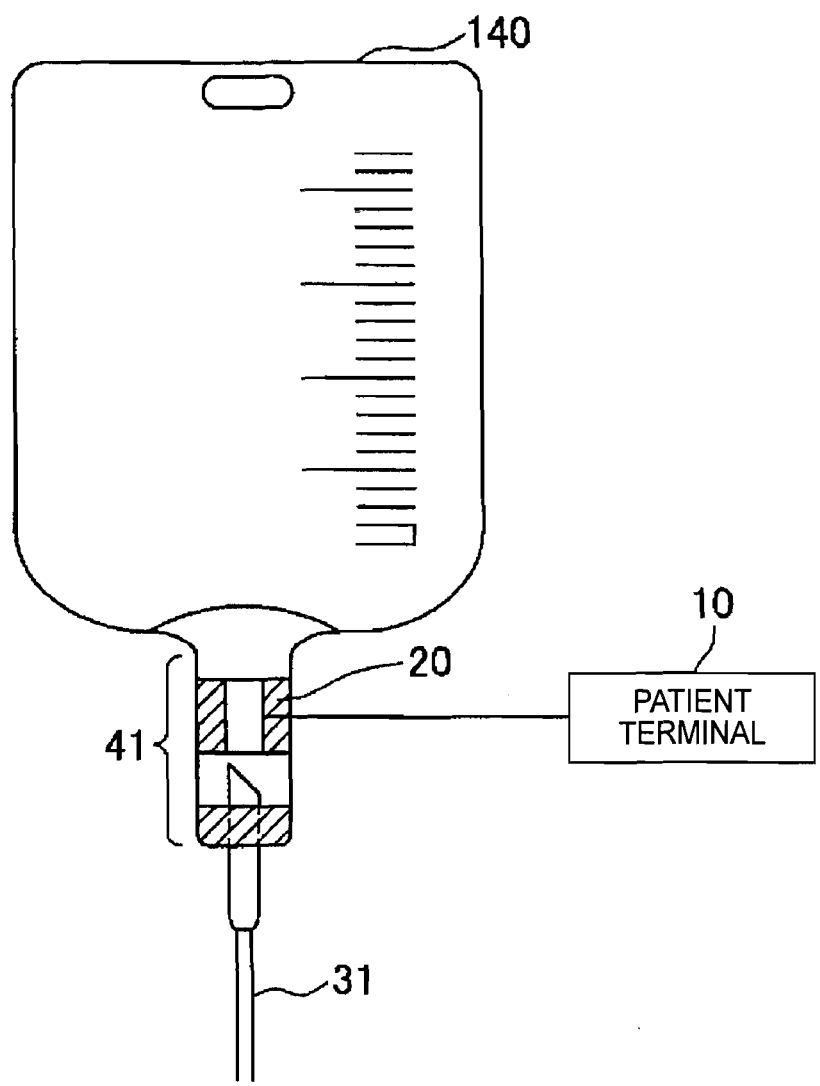
FIG. 21 depicts an infusion pump system according to a third embodiment of the present invention.

Referring to FIG. 21, the infusion pump system 4 includes an infusion bag 140 serving as the medical solution container; an infusion set 30 (i.e., infusion tube 31) serving as the infusion line, a not-shown flowmeter; and a patient terminal 10.

The infusion bag 140 is a medical solution container configured to contain the medical solution for infusion into the infusion target (i.e., patient) H. The infusion bag 140 is made of flexible synthetic resin and has a shape of a bag, at an end of which there is provided a medical solution exit portion 41 which is a passage for drawing out the medical solution contained therein. The infusion tube 31 is attached to the medical solution exit portion 41 such that the medical solution is drawn out of the infusion bag 140 via the infusion tube 31.

Also, there is provided an infusion pump 20 inside of the medical solution exit portion 41 and inward of the section thereof where the infusion tube 31 is attached to the medical solution exit portion 41. The infusion pump 20 has the same configuration as that of the infusion pump 20 in the first embodiment, description of which is omitted. The infusion pump 20 provided in the infusion bag 140 and the not-shown flowmeter are connected to the patient terminal 10. Since the configuration and modes of control of the patient terminal 10 are the same as those in the first embodiment, explanation is omitted.

In this manner, the infusion pump 20 according to the present invention is provided inside of the medical solution exit portion 41 and inward of the section thereof at which the infusion tube 31 is attached to the infusion bag 140. Accordingly, it is possible to use a conventional infusion set (infusion tube) used heretofore in conventional infusion pump systems and conventional infusion sets, as a result of which it is possible to take advantage of existing assets such as the conventional infusion set. Also, the operation of replacing the air inside of the infusion pump by the medical solution (which is also called "priming") may be omitted.

Also, heretofore, the piezoelectric pumps have an open structure. When the infusion pump comprising the piezoelectric pump is provided midway in the infuse infusion set, the difference between the fluid level of the medical solution and the altitude of the infusion pump acts as the force causing delivery of the medical solution, as a result of which a certain amount of the medical solution may unintentionally flow out in the absence of the operation of the infusion pump. In contrast, according to the present invention, it is possible to reduce the difference between the fluid level of the medical solution and the altitude of the infusion pump, and thus prevent the medical solution from flowing out while the infusion pump is not operated.

It should be noted that although the above-described embodiment employs the infusion pump provided inside of the infusion bag, the present invention is not limited to this specific configuration. For example, the infusion tube may be provided in one piece with the infusion bag.

Figure 22:
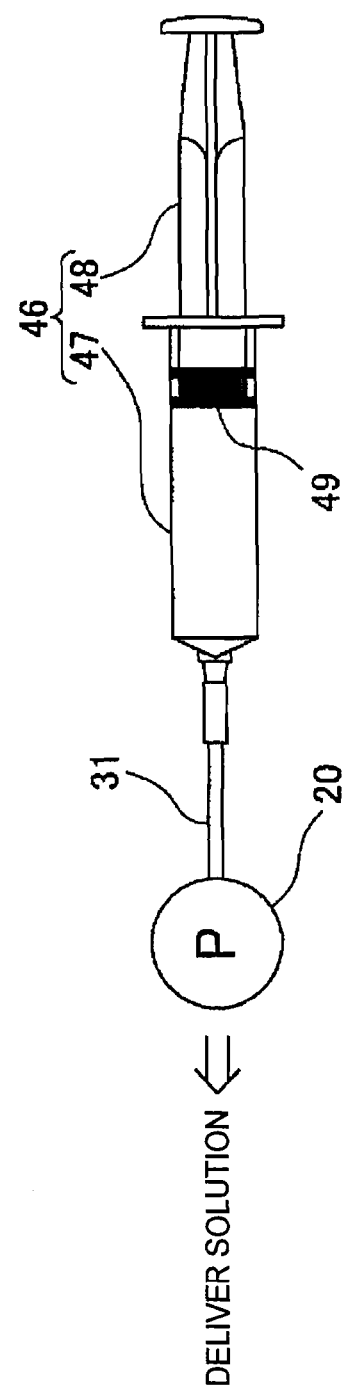
FIG. 22 depicts an exemplary configuration of the infusion pump system that includes a syringe pump serving as a medical solution container.

A syringe pump 46 illustrated in FIG. 22 may be conventionally used in infusion pump systems as the medical solution container. The syringe pump 46 includes a cylinder 47 containing the medical solution and a plunger 48 configured to push out the medical solution contained in the cylinder 47. By virtue of the syringe pump 46 with this configuration, it is possible to manually draw the medical solution by pressing the plunger 48 toward the cylinder 47, which facilitates the priming. However, there is a problem in a case where an attempt is made to draw the medical solution from the syringe pump 46 using the above-described infusion pump 2.

Specifically, since the infusion pump is constructed to make suction by negative pressure to draw the medical solution, the medical solution is drawn out as the force for suction of the medical solution by the negative pressure exceeds the frictional force between the water-tight portion 49 of the plunger 48 and the inner surface of the cylinder 47. The negative pressure will decrease in the course of drawing out of the medical solution. The force for suction of the medical solution by the negative pressure again exceeds the frictional force, then the medical solution will be again drawn out. It is appreciated that a pulsating flow occurs in the medical solution as a result of the repetition of the above-described operation.

To address this problem, as illustrated in FIG. 23, there are provided a cylinder 42 configured to accommodate the infusion bag 140 therein and a plunger 43 configured to compress the infusion bag 140 accommodated in the cylinder 42. Further, the cylinder 42 includes an air hole 42a by which the inside of the cylinder 42 and the outside thereof are in communication with each other. The air hole 42a has a filter configured to prevent entry of foreign matters into the cylinder 42. This configuration allows the medical solution to be manually delivered, in the absence of the operation of the infusion pump 20, by manually pressing the plunger 43 into the cylinder 42, which facilitates priming operation, and air can be drawn into the cylinder 42 via the air hole 42a, so that suction of the medical solution is not prevented by the above-described frictional force, and thus pulsating flow of the medical solution can be effectively prevented.

It should be noted that although the infusion pump in the above-described embodiments comprises the piezoelectric pump unit, the present invention may incorporate infusion pumps having other driving systems. Nevertheless, a disposable the infusion pump including the piezoelectric pump unit is desirable in view of reduction in size and costs.

Also, while the MEMS industry in general is oriented toward development of systems for delivering fluids in small amount with high accuracy, the present invention contemplates applications of the piezoelectric pump in the fields that involve infusion of fluids to be made with both high capacity and high accuracy, and the medical field is the most popular one among such fields. However, the present invention will also find other applications in the technical fields where application of fluid dynamics finds its place, for example, amongst others, fuel control for aircrafts and automobiles.

It should be noted that the embodiment has only been illustrated as a typical one of the present invention, and the present invention is in no way limited to the illustrated embodiment. Hence, the present invention can be effectuated with various modifications made thereto within the scope of the present invention.

The invention claimed is:

1. An infusion pump system for infusion of a predetermined medical solution at a preset reference infusion speed, comprising:
   (A) a medical solution container configured to contain a medical solution;
   (B) an infusion line via which the medical solution is drawn from the medical solution container;
   (C) an infusion pump configured to discharge the medical solution via the infusion line from the medical solution container directly into a body of a patient;
   (D) a reference infusion speed storing unit configured to store a reference infusion speed;
   (E) a correction coefficient storing unit configured to store a correction coefficient for use in correction of a variation in a discharge speed of the medical solution, the correction coefficient being predefined in accordance with a degree of medical effect of the medical solution;
   (F) an infusion speed measurement unit configured to measure an infusion speed of the medical solution flowing through the infusion line;
   (G) a discharge speed computation unit configured for discharge speed computation to compute a discharge speed of the infusion pump for infusion of the medical solution at the reference infusion speed, the discharge speed determined with reference to (i) a current discharge speed of the infusion pump, (ii) the reference infusion speed stored in the reference infusion speed storing unit, and (iii) the infusion speed of the medical solution measured by the infusion speed measurement unit;
   (H) a discharge speed correction unit configured for discharge speed correction to correct the discharge speed that has been obtained as a result of the discharge speed computation by the discharge speed computation unit, the discharge speed correction being made with reference to (i) the current discharge speed of the infusion pump and (ii) the correction coefficient for the medical solution stored in the correction coefficient storing unit; and
   (I) a control unit configured to control the infusion pump to make the infusion pump discharge the medical solution at the discharge speed obtained as a result of the discharge speed correction by the discharge speed correction unit.

2. The infusion pump system according to claim 1, further comprising:
   an information input unit into which information on an infusion target into which the medical solution is infused is input;
   a medical solution information storing unit configured to store usage and dosage of the medical solution;
   an infusion speed range computation unit configured for infusion speed range computation to compute an allowable range of the infusion speed for the medical solution, the infusion speed range computation being made with reference to (i) the information input into the information input unit and (ii) the usage and dosage of the medical solution stored in the medical solution information storing unit; and
   a safe operation unit configured to perform a predefined safe operation when the discharge speed corrected by the discharge speed correction unit does not fall within the allowable range of the infusion speed for the medical solution computed by the infusion speed range computation unit.

3. The infusion pump system according to claim 2, wherein the safe operation unit is configured to trigger an alarm.

4. The infusion pump system according to claim 2, wherein the safe operation unit is configured to control the infusion pump to make the infusion pump discharge the medical solution at the discharge speed corrected by the discharge speed correction unit.

5. The infusion pump system according to claim 2, wherein the safe operation unit is configured to halt the infusion pump discharging the medical solution.

6. The infusion pump system according to claim 1, wherein the infusion pump includes a piezoelectric pump unit comprising at least one piezoelectric pump driven by a piezoelectric element.

7. The infusion pump system according to claim 6, wherein the infusion pump includes a plurality of the piezoelectric pump units arranged in parallel with each other; a plurality of entry tubes via which the piezoelectric pump units are individually connected to the infusion line, the entry tubes having a cross section smaller than that of the infusion line; and a bypass tube configured to connect the entry tubes to each other.

8. The infusion pump system according to claim 7, wherein the infusion pump comprises a plurality of groups of the piezoelectric pump units, and the control unit is configured to use different discharge timings to individually control the groups of the piezoelectric pump units.

9. The infusion pump system according to claim 6, further comprising:
a plurality of the medical solution containers each containing a corresponding each of a plurality of the medical solutions;
a plurality of the infusion lines via each of which a corresponding each of the medical solutions is drawn out of the corresponding each of the medical solution containers; wherein the infusion pump includes one piezoelectric pump unit and a plurality of the entry tubes each connecting a corresponding each of the infusion lines to the piezoelectric pump unit, and a plurality of cut-off valves each provided in a corresponding each of the entry tubes and configured to block the medical solution drawn via the infusion line into the piezoelectric pump unit, and the control unit is configured to control opening and closing of the cut-off valves such that predefined amounts of the medical solutions are drawn into the piezoelectric pump unit from corresponding each of the entry tubes.

10. The infusion pump system according to claim 9, wherein the control unit is configured to close one of the cut-off valves when a predefined negative pressure avoidance time has elapsed after opening of another of the cut-off valves.

11. The infusion pump system according to claim 9, wherein the control unit is configured to intermittently open and close at least one of the cut-off valves each provided in corresponding each of the entry tubes.

12. The infusion pump system according to claim 9, further comprising a biometric information input unit into which biometric information is input, the biometric information being measured in the infusion target into which the medical solution is infused, wherein the control unit is configured to open and close a selected one of the cut-off valves on the basis of the biometric information input to the biometric information input unit.

13. The infusion pump system according to claim 1, further comprising a bypass unit configured to discharge the medical solution via the infusion line, the bypass unit bypassing the infusion pump.

14. The infusion pump system according to claim 1, wherein the infusion pump is arranged inside of the medical solution container such that the infusion pump is positioned inward with reference to the medical solution exit portion via which the infusion line is attached to the medical solution container.

15. The infusion pump system according to claim 14, further comprising a cylinder accommodating therein a medical solution container made of a flexible material; and a plunger configured to compress the medical solution container accommodated in the cylinder, the cylinder including an air hole via which an inside thereof and an outside thereof are in communication with each other.

16. The infusion pump system according to claim 1, further comprising a deaerating unit provided downstream of the infusion pump and configured to remove an air bubble in the infusion line.

17. The infusion pump system according to claim 1, further comprising a condition input unit into which condition information is input, the condition information being indicative of a condition of the infusion target into which the medical solution is infused;
an information storing unit connected to the condition input unit via a communications device and configured to store the condition information input into the condition input unit; and
at least one information terminal unit connected to the information storing unit and configured to reference the condition information stored in the information storing unit.

18. An infusion pump system for infusion of a predetermined medical solution within a predefined infusion completion time, comprising:
(A) a medical solution container configured to contain a medical solution,
(B) an infusion line via which the medical solution is drawn from the medical solution container;
(C) an infusion pump configured to discharge the medical solution via the infusion line from the medical solution container directly into a body of a patient;
(D) a correction coefficient storing unit configured to store a correction coefficient for use in correction of a variation in a discharge speed of the medical solution, the correction coefficient being predefined in accordance with a degree of medical effect of the medical solution;
(E) a remaining amount detection unit configured to detect a remaining amount of the medical solution;
(F) a remaining time measurement unit configured to measure a remaining time before the infusion completion time is reached;
(G) a discharge speed computation unit configured for discharge speed computation to compute a discharge speed of the infusion pump for infusion of the medical solution within the infusion completion time, the discharge speed computation being made with reference to (i) the remaining amount of the medical solution detected by the remaining amount detection unit and (ii) the remaining time before the infusion completion time is reached measured by the remaining time measurement unit;
(H) a discharge speed correction unit configured for discharge speed correction to correct the discharge speed obtained as a result of the discharge speed computation by the discharge speed computation unit, the discharge speed correction being made with reference to (i) a current discharge speed of the infusion pump and (ii) the correction coefficient for the medical solution stored in the correction coefficient storing unit; and
(I) a control unit configured to control the infusion pump to make the infusion pump discharge the medical solution at the discharge speed that has been obtained as a result of the discharge speed correction by the discharge speed correction unit.

* * * * *